United States Patent [19]

Chen et al.

[11] Patent Number: 4,640,704
[45] Date of Patent: Feb. 3, 1987

[54] HERBICIDAL SULFONAMIDES

[75] Inventors: Chi-wan Chen, Silver Spring, Md.; Gregory W. Schwing, Lincoln University, Pa.

[73] Assignee: E. I. Du Pont de Nemours and Company, Wilmington, Del.

[21] Appl. No.: 790,305

[22] Filed: Oct. 22, 1985

Related U.S. Application Data

[60] Division of Ser. No. 637,580, Aug. 3, 1984, Pat. No. 4,582,525, which is a continuation-in-part of Ser. No. 168,346, Jul. 11, 1980, abandoned.

[51] Int. Cl.[4] .................... C07D 239/70; A01N 47/36
[52] U.S. Cl. ......................................... 71/92; 544/253; 544/278
[58] Field of Search .................... 544/253, 278; 71/92

[56] References Cited

U.S. PATENT DOCUMENTS 4,537,618  8/1985  Shorter .................................. 71/92

Primary Examiner—Robert Gerstl

[57] ABSTRACT

This invention relates to N-(heterocyclicaminocarbonyl)-o-alkenylbenzenesulfonamides which are useful as agricultural chemicals.

10 Claims, No Drawings

HERBICIDAL SULFONAMIDES

This is a division of application Ser. No. 637,580, filed Aug. 3, 1984 now U.S. Pat. No. 4,582,525 which is a continuation-in-part of my copending application Ser. No. 168,346, filed July 11, 1980 now abandoned.

BACKGROUND OF THE INVENTION

This invention relates to novel N-(heterocyclicaminocarbonyl)-o-alkenylbenzenesulfonamides which are useful as agricultural chemicals and in particular as herbicides and growth regulants.

Netherlands Pat. No. 121,788, published Sept. 15, 1966, teaches the preparation of compounds of Formula (I) and their use as general or selective herbicides:

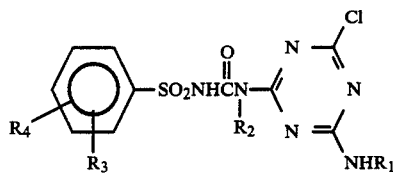

wherein
$R_1$ and $R_2$ may independently be alkyl of 1-4 carbon atoms; and
$R_3$ and $R_4$ may independently be hydrogen, chlorine or alkyl of 1-4 carbon atoms.

Compounds of Formula (II), and their use as antidiabetic agents, are reported in J. Drug. Res. 6, 123 (1974):

wherein R is pyridyl.

In U.S. Pat. No. 4,127,405, compounds are disclosed of the general formula:

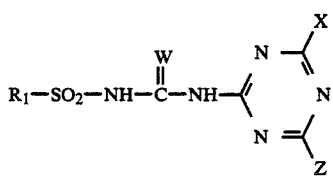

wherein
$R_1$ is

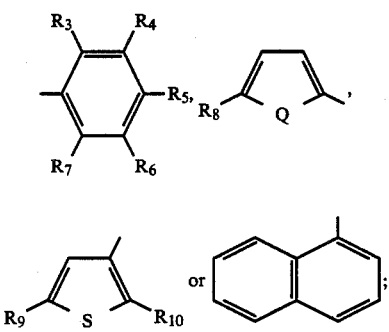

$R_3$ and $R_6$ are independently hydrogen, fluorine, chlorine, bromine, iodine, alkyl of 1-4 carbon atoms, alkoxy of 1-4 carbon atoms, nitro, trifluoromethyl, cyano, $CH_3S(O)_n$— or $CH_3CH_2S(O)_n$—;

$R_4$ is hydrogen, fluorine, chlorine, bromine or methyl;

$R_5$ is hydrogen, fluorine, chlorine, bromine, methyl or methoxy;

$R_7$ is hydrogen, fluorine, chlorine, bromine, alkyl of 1-2 carbon atoms or alkoxy of 1-2 carbon atoms;

$R_8$ is hydrogen, methyl, chlorine or bromine;

$R_9$ and $R_{10}$ are independently hydrogen, methyl, chlorine or bromine;

W and Q are independently oxygen or sulfur;

n is 0, 1 or 2;

X is hydrogen, chlorine, bromine, methyl, ethyl, alkoxy of 1-3 carbon atoms, trifluoromethyl, $CH_3S$— or $CH_3OCH_2$—; and Z is methyl or methoxy; or their agriculturally suitable salts; provided that:

(a) when $R_5$ is other than hydrogen, at least one of $R_3$, $R_4$, $R_6$ and $R_7$ is other than hydrogen and at least two of $R_3$, $R_4$, $R_6$ and $R_7$ must be hydrogen;

(b) when $R_5$ is hydrogen and all of $R_3$, $R_4$, $R_6$ and $R_7$ are other than hydrogen, then all of $R_3$, $R_4$, $R_6$ and $R_7$ must be either chlorine or methyl; and (c) when $R_3$ and $R_7$ are both hydrogen, at least one of $R_4$, $R_5$ or $R_6$ must be hydrogen.

In particular, the patent discloses orthosubstituted compounds wherein the substitution is $C_1$–$C_4$ alkyl.

The presence of undesired vegetation causes substantial damage to useful crops, especially agricultural products that satisfy man's basic food needs, such as soybeans, corn, wheat and the like. The current population explosion and concomitant world food shortage demand improvements in the efficiency of producing these crops. Preventing or minimizing the loss of a portion of such valuable crops by killing, or inhibiting the growth of undesired vegetation is one way of improving this efficiency.

A wide variety of materials useful for killing, or inhibiting (controlling) the growth of undesired vegetation is available; such materials are commonly known as herbicides. The need exists however, for still more effective herbicides especially those which destroy or retard weeds without causing significant damage to useful crops.

SUMMARY OF THE INVENTION

This invention relates to novel compounds of Formula I, suitable agricultural compositions containing them, and their method of use as general, as well as selective, pre-emergence and post-emergence herbicides.

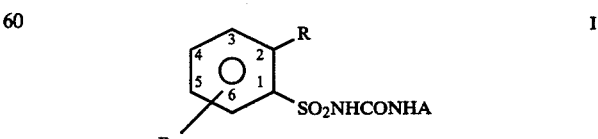

wherein
R is

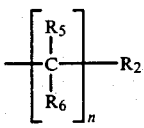

$R_2$ is $C_2$–$C_5$ alkenyl, $C_5$–$C_6$ cycloalkenyl or $C_2$–$C_3$ alkenyl substituted with 1–3 chlorine atoms;
n is 0 or 1;
$R_1$ is H, F, Cl, Br, $NO_2$, $CF_3$, $C_1$–$C_4$ alkyl, $OCF_3$ or $C_1$–$C_3$ alkoxy;
$R_5$ and $R_6$ are independently H or $CH_3$;
A is

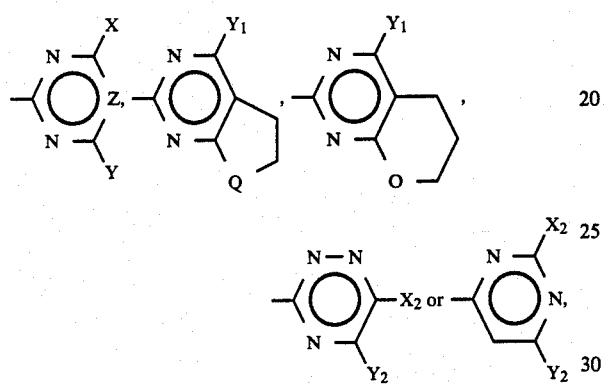

X is H, $CH_3$, $OCH_3$, $OCH_2CH_3$, $OCH_2CF_3$, $CH_2OCH_3$ or Cl;
Y is $CH_3$, $OCH_3$, $OCH_2CH_3$, $NH_2$, $NHCH_3$ or $N(CH_3)_2$;
Z is N, CH, CCl, CBr, CCN, $CCH_3$, $CCH_2CH_3$, $CCH_2CH_2Cl$ or $CCH_2CH=CH_2$;
$Y_1$ is H, $CH_3$, $OCH_3$ or Cl;
$X_2$ and $Y_2$ are independently $CH_3$ or $OCH_3$; and
Q is O or $CH_2$;
provided that
(1) when Z is other than N or CH, then X is H, $CH_3$ or $OCH_3$ and Y is $CH_3$ or $OCH_3$; and
(2) when Z is N and X is Cl, then Y is $CH_3$.

PREFERRED COMPOUNDS

Preferred for their higher herbicidal activity and/or more favorable ease of synthesis are:
(1) Compounds of Formula I wherein $R_1$ is H;
(2) Compounds of Preferred (1) wherein A is

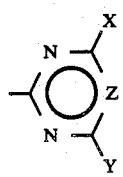

and Z is N or CH;
(3) Compounds of Preferred (2) wherein $R_5$ and $R_6$ are H; and
(4) Compounds of Preferred (3) wherein X is $CH_3$, $OCH_3$ $OCH_2CH_3$ or $CH_2OCH_3$, and Y is $CH_3$ or $OCH_3$.

Specifically preferred for highest herbicidal activity and/or more favorable ease of synthesis are:

N-[(4,6-dimethylpyrimidin-2-yl)aminocarbonyl]-2-(1-methylethenyl)benzenesulfonamide;
N-[(4-methoxy-6-methylpyrimidin-2-yl)aminocarbonyl]-2-(1-methylethenyl)benzenesulfonamide;
N-[(4,6-dimethoxypyrimidin-2-yl)aminocarbonyl]-2-(1-methylethenyl)benzenesulfonamide;
N-[(4-methoxy-6-methyl-1,3,5-triazin-2-yl)aminocarbonyl]-2-(1-methylethenyl)benzenesulfonamide;
N-[(4,6-dimethoxy-1,3,5-triazin-2-yl)aminocarbonyl]-2-(1-methylethenyl)benzenesulfonamide;
N-[(4,6-dimethyl-1,3,5-triazin-2-yl)aminocarbonyl]-2-(1-methylethenyl)benzenesulfonamide;
2-(1-cyclopentenyl)-N-[(4,6-dimethylpyrimidin-2-yl)aminocarbonyl]benzenesulfonamide;
2-(1-cyclopentenyl)-N-[(4-methoxy-6-methylpyrimidin-2-yl)-aminocarbonyl]benzenesulfonamide;
2-(1-cyclopentenyl)-N-[(4,6-dimethoxypyrimidin-2-yl)amino-carbonyl]benzenesulfonamide; 2-(1-cyclopentenyl)-N-[(4-methoxy-6-methyl-1,3,5-triazin-2-yl)aminocarbonyl]benzenesulfonamide; and
2-(1-cyclopentenyl)-N-[(4,6-dimethoxy-1,3,5-triazin-2-yl)aminocarbonyl]benzenesulfonamide.

This invention also relates to compounds of Formula II and Formula III which are useful as intermediates for the preparation of the herbicidal compounds of Formula I

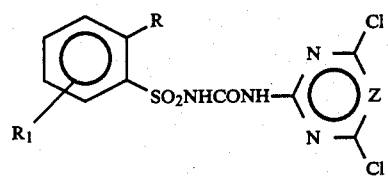

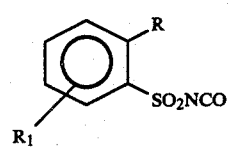

wherein
R is

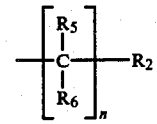

$R_2$ is $C_2$–$C_5$ alkenyl, $C_5$–$C_6$ cycloalkenyl or $C_2$–$C_3$ alkenyl substituted with 1–3 chlorine atoms;
n is 0 or 1;
$R_1$ is H, F, Cl, Br, $NO_2$, $CF_3$, $C_1$–$C_4$ alkyl, $OCF_3$ or $C_1$–$C_3$ alkoxy;
$R_5$ and $R_6$ are independently H or $CH_3$; and
Z is N or CH.

PREFERRED INTERMEDIATES

Preferred intermediates, for the higher herbicidal activity of the compounds of Formula I, are the compounds of Formula II and Formula III where $R_1$ is H.

DETAILED DESCRIPTION OF THE INVENTION

Synthesis

The compounds of Formula I can be prepared by one or more of the following methods; the first and most general of which is shown in Equation 1. In this procedure, an aryl sulfonylisocyanate of Formula III is combined with an appropriate aminoheterocycle IV wherein R, $R_1$ and A are as previously defined.

Equation 1

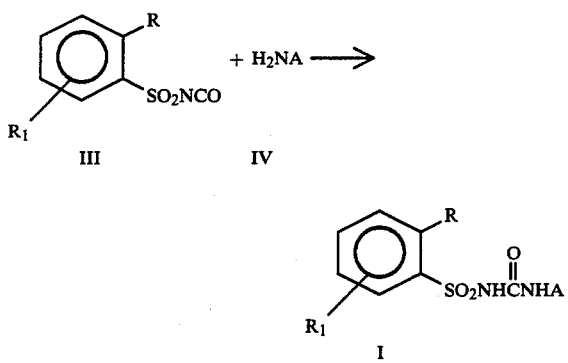

The reaction is best carried out in inert aprotic organic solvents such as methylene chloride, tetrahydrofuran or acetonitrile, at ambient temperature and pressure. The mode of addition is not critical; however, it is often convenient to add the sulfonyl isocyanate to a stirred suspension of the aminoheterocycle. Since such isocyanates are usually liquids, their addition can be easily controlled.

The reaction is generally exothermic. In some cases, the desired product is insoluble in the warm reaction mixture and crystalline from it in pure form. Products soluble in the reaction medium are isolated by evaporation of solvent, trituration of the solid residue with solvents such as 1-chlorobutane or ethyl ether, and filtration.

An alternative method of synthesis is shown in Equation 2, wherein Z is CH or N, X' is $CH_3O$ or $C_2H_5O$, and Y' is $CH_3O$ or $C_2H_5O$. The intermediate II is formed upon reaction of an appropriate sulfonamide of Formula V with a heterocyclic isocyanate of Formula VI. This intermediate can then be treated with an excess of an alkali metal alkoxide to produce chloro alkoxy heterocyclic ureas such as VII or, upon further treatment, the dialkoxyheterocyclic ureas VIII.

Equation 2

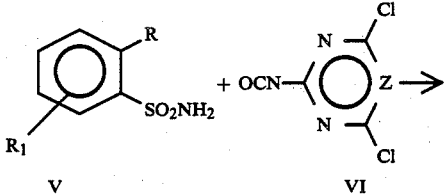

-continued
Equation 2

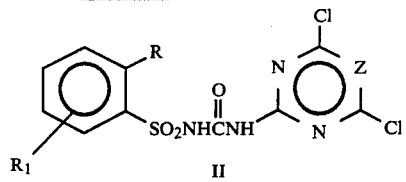

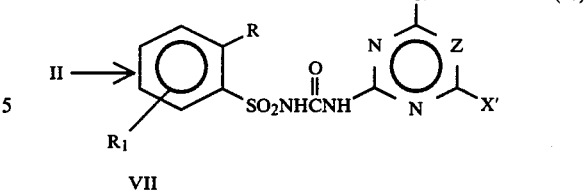

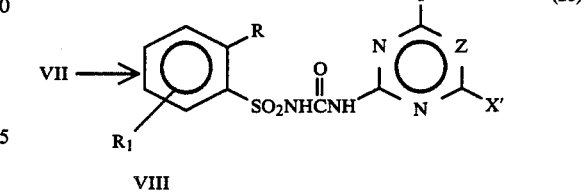

The heterocyclic isocyanates (VI) used in Reaction 2a may be prepared according to the methods described in Swiss Pat. No. 579,062, U.S. Pat. No. 3,919,228, U.S. Pat. No. 3,732,223 and Agnew. Chem. Int. Ed. 10, 402 (1976), the disclosures of which are herein incorporated by reference.

Thus the aromatic sulfonamide V and the heterocyclic isocyanate VI are contacted in the presence of an inert organic solvent, for example, acetonitrile, tetrahydrofuran (THF), toluene, acetone or butanone. Optionally, a catalytic amount of a base, such as 1,4-diazabicyclo[2.2.2]octane (DABCO), potassium carbonate, sodium hydride or potassium tert-butoxide, may be added to the reaction mixture. The quantity of base constituting a catalytic amount would be obvious to one skilled in the art. The reaction mixture is preferably maintained at a temperature of about 25° to 110° C., and the product can generally be recovered by cooling and filtering the reaction mixture. For reasons of efficiency and economy, the preferred temperature range is about 60° to 85° C.

In Reaction Steps 2b and 2c, one or two of the halogen atoms on the heterocyclic ring of the compound of Formula II is displaced by a nucleophilic species. Generally, this may be done by contacting the compound of Formula II either with alkanol or with alkoxide as described by X', where X' is methoxy or ethoxy.

Thus, in Reaction Step 2b, a compound of Formula II, can be contacted with at least one equivalent of alkanol. This reaction is sluggish, however, and it is preferred to contact the compound of Formula II with at least two equivalents of alkoxide. The alkoxide can be provided in a number of ways.

(a) The compound of Formula II can be suspended or dissolved in an alkanol solvent in the presence of at least two equivalents of alkoxide. The alkoxide can be added directly as alkali metal or alkaline earth metal alkoxide or can be generated by the addition to the alkanol solvent of at least two equivalents of a base capable of generating alkoxide from the solvent. Suitable bases include, but are not limited to, the alkali and alkaline earth metals, their hydrides and tert-butoxides. For example, when X' is methoxy, the compound of Formula II could be suspended or dissolved in methanol in the presence of two equivalents of sodium methoxide. Alternatively, two equivalents of sodium hydride could be used in place of the sodium methoxide.

(b) The compound of Formula II can be suspended or dissolved in an inert solvent in the presence of at least two equivalents of alkoxide. Suitable inert solvents include, but are not limited to, acetonitrile, THF and dimethylformamide. The alkoxide may be added directly as alkali metal or alkaline earth metal alkoxide or may be generated from alkanol and a base as described in (a) above. For example, when X' is methoxy, the compound of Formula II could be suspended or dissolved in THF in the presence of two equivalents of sodium methoxide. Alternatively, two equivalents each of methanol and sodium hydride could be used instead of sodium methoxide.

For reasons of economy and efficiency, procedure (a) is the more preferred method.

It should be noted that two equivalents of alkoxide are required for Reaction Step (b) whereas only one equivalent of alkanol is needed for the same process. This difference is due to the reaction which is believed to occur between the alkoxide and the sulfonyl nitrogen of the sulfonamide of Formula II. When alkoxide is used, the first equivalent of alkoxide removes a proton from the sulfonyl nitrogen, and is only the second equivalent which effects displacement of the halogen. As a result, two equivalents of alkoxide are required. The resulting salt must be acidified, e.g., with sulfuric, hydrochloric or acetic acid, to yield a compound of Formula VII. Applicant, of course, does not intend to be bound by the mechanism described above.

In Reaction Step 2c a compound of Formula VII is contacted with either one equivalent of alkanol, or with two equivalents of alkoxide. When alkoxide is used, it may be provided in either of the methods described above in connection with Reaction Step 2b and the resulting salt can be acidified to yield a compound of Formula VIII, wherein Y' is methoxy or ethoxy.

When $X'=Y'=OCH_3$ or $OC_2H_5$ Reaction Steps 2b and 2c may be combined. Thus, a compound of Formula II may be contacted either with at least two equivalents of alkanol or with at least three equivalents of alkoxide.

For a compound of Formula II, certain reaction conditions will favor displacement of only one of the chloro groups. These conditions are the use of low temperatures, and when alkoxide is used, the slow addition of the stoichiometric amount of alkoxide or alkoxide-generating base to the medium containing the compound of Formula II.

When alkoxide is used, both Reaction Steps 2b and 2c are preferably run at temperatures within the range of about $-10°$ to $80°$ C., the range of about $0°$ to $25°$ C. being more preferred. Reaction Steps 2b and 2c are more sluggish when alkanol is used instead of alkoxide, and more drastic conditions are required for the reaction to go to completion. Thus, higher temperatures, up to and including the boiling point of the alkanol itself, are required.

Another method of synthesis of compounds of Formula I is outlined in Equation 3, in which $R_1$, $R_5$, $R_6$ and n are as previously defined, and $R_7$ and $R_8$ are independently hydrogen or $C_1$-$C_3$ alkyl.

Equation 3

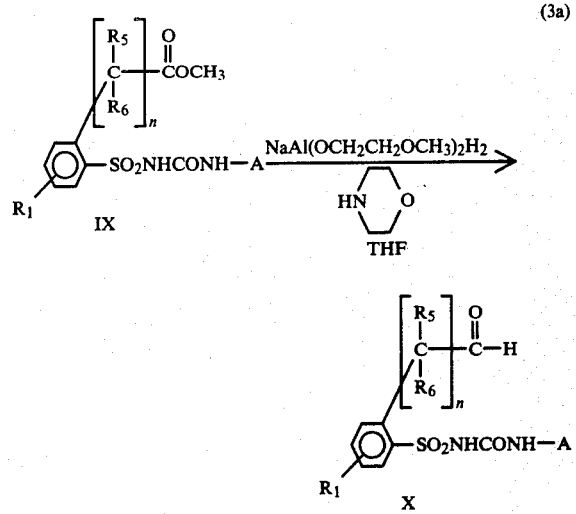

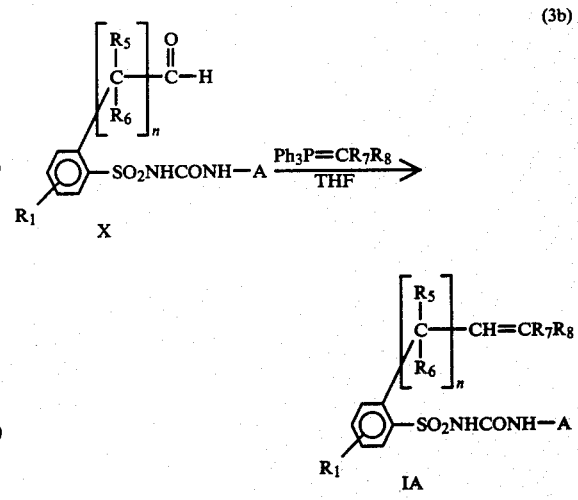

The syntheses of compounds IX with n=0 have been disclosed in unexamined European Pat. No. 7687 and those with n=1 have been disclosed in copending application BA-8369-A, both of which are herein incorporated by reference.

Reduction of ester IX to the corresponding aldehyde X may be accomplished by the use of sodium bis(2-methoxyethoxy)aluminum hydride in the presence of morpholine as described in the teaching of R. Kanazawa et al., *Synthesis*, 526 (1976). The reaction is carried out typically at about $-40°$ C. in an inert organic solvent, preferably tetrahydrofuran, and isolated from the unreacted ester and the over-reduced alcohol by column chromatography.

The aldehyde X is then converted to the o-alkenylbenzenesulfonylurea IA with an excess of the appropriately substituted Wittig reagent, a method known in the art for the synthesis of olefins from aldehydes as described in *Organic Synthesis*, coll. vol. V, 361, 751, and reviewed in *Organic Reactions*, 14, 270 (1965).

Additional claimed compounds of Formula IB, where $R_2$ is a more highly branched $C_3$-$C_5$ alkenyl, may be synthesized from their corresponding ketones XII, which are in turn obtained from sulfonylureas IX, as indicated in Equation 4.

Equation 4

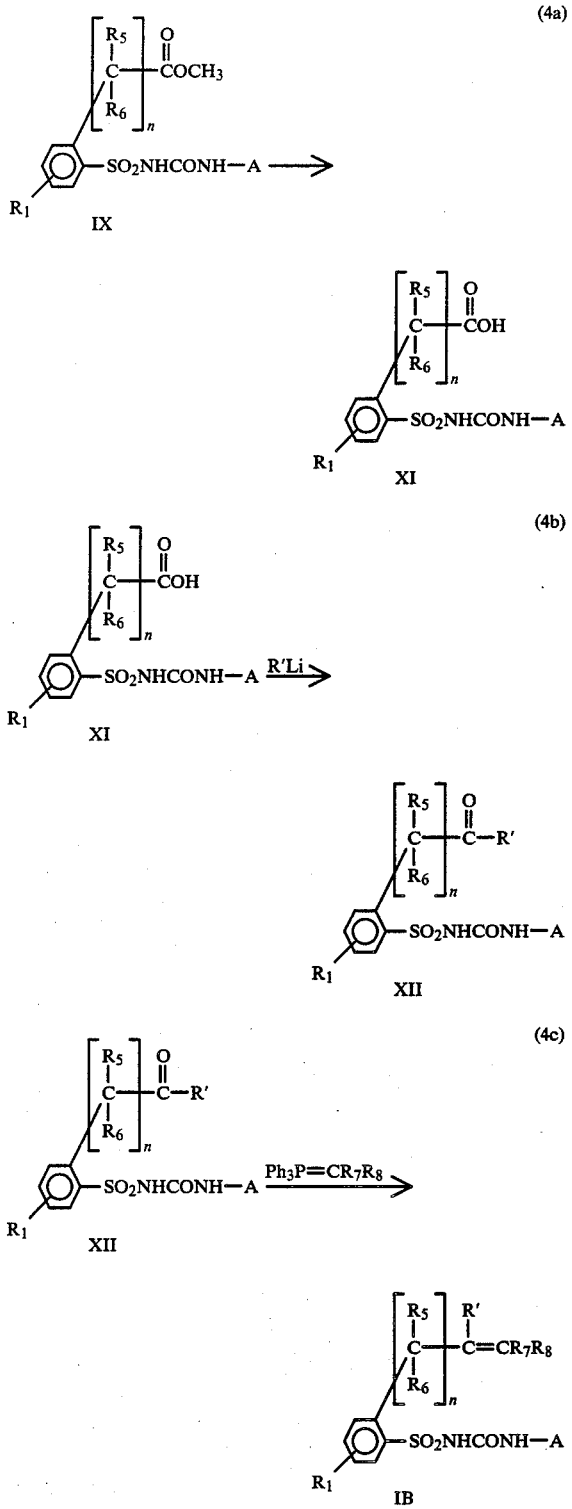

wherein R' is $C_1$-$C_3$ alkyl and $R_7$ and $R_8$ are independently hydrogen or methyl.

The first step involves hydrolysis of ester IX to acid XI with potassium hydroxide in ethanol/water, or with potassium t-butoxide in dimethyl sulfoxide when A is a triazine substituted with alkoxy group(s).

The reaction of an organolithium compound with a carboxylic acid to yield a ketone is well known in the literature, e.g., H. Gilman and P. R. Van Ess, *JACS*, 55, 1258 (1933); H. Gilman, W. Langham and F. W. Moore, ibid, 62, 2327 (1940); C. Tegner, *Chem. Scand.*, 6, 782 (1952); J. F. Arens and D. A. Van Dorp, Rec. Trav., 65, 338 (1946); 66, 759 (1947); and C. H. DePuy, J. M. Dappen, K. L. Eilers and R. A. Klein, *J. Org. Chem.*, 2813 (1964). This conversion is carried out with a large excess of the organolithium compound in a suitable solvent such as tetrahydrofuran at room temperature.

The resulting ketone XII is then reacted with a Wittig reagent to afford compound IB in a similar manner to that described in Equation 3.

SULFONYLISOCYANATE INTERMEDIATES

The intermediate sulfonyl isocyanates of Formula III can be prepared by reacting corresponding sulfonamides (V) with phosgene in the presence of n-butyl isocyanate at reflux in a solvent such as chlorobenzene, according to the procedure of H. Ulrich and A. A. Y. Sayigh, *Newer Methods of Preparative Organic Chemistry*, Vol. VI, p. 223-241, Academic Press, New York and London, W. Forest Ed. Alternatively, the process of Ulrich and Sayigh can be varied by the addition of a tertiary amine, such as, triethylamine or DABCO, to the reaction mixture. The preparation of sulfonamides (V) from ammonium hydroxide and sulfonyl chlorides is widely reported in the literature, e.g. Crossley et. al. *J. Am. Chem. Soc.*, 60, 2223 (1938).

Preparation of the corresponding sulfonyl chlorides in which R is cycloalkenyl is best accomplished starting from the sulfonic acid salt XIII as shown in Equation 5, wherein m=1 or 2, and $R_1$ is as defined above.

Equation 5

-continued
Equation 5

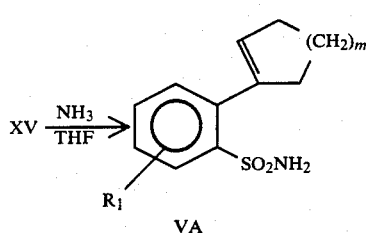

(5c)

In reaction (5a) a substituted benzenesulfonic acid salt is contacted with a slight excess of an alkyllithium reagent such as n-butyllithium at 0° to 50° C., preferably below ambient temperature, and in an inert aprotic solvent such as tetrahydrofuran (THF). After allowing this mixture to stir at ambient temperature for approximately one hour, it is cooled in an ice bath and contacted slowly with a slight excess of the appropriate ketone then allowed to stir at ambient temperature overnight. The dilithium salt (XIV) normally precipitates from the mixture and is collected by filtration and dried.

The product obtained from reaction (5a), may then be converted to the alkenylsulfonyl chloride XV by reacting XIV with a 10 to 20 fold excess of thionyl chloride containing a catalytic amount of N,N-dimethylformamide (1% is conveniently used) at 0° to 10° C., preferably. After 1 hour the reaction is normally complete and is then warmed to room temperature, filtered to remove inorganic by-products and the filtrate is evaporated under reduced pressure.

Conversion of the crude product XV into the desired sulfonamide VA can be accomplished using the standard procedures mentioned above, for example, by dissolving XV in THF and adding an excess of concentrated aqueous ammonia.

This procedure outlined in Equation 5 may also be used to prepare acyclic 2-alkenylarylsulfonamides from acyclic ketones and the appropriate benzenesulfonic acid salt (XIII).

An additional synthesis of sulfonamides V which may also be used as precursors to isocyanates of Formula III is presented in Equation 6, wherein R' is hydrogen or methyl, and M is an alkali metal.

Equation 6

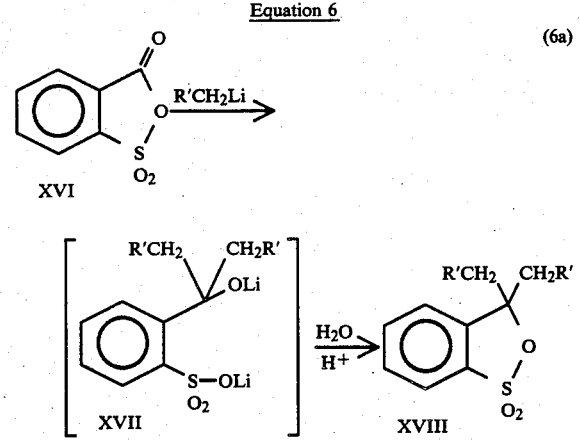

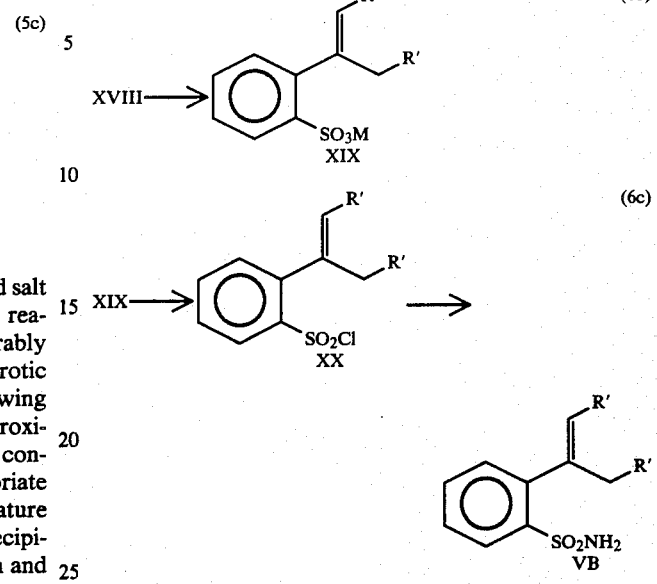

Commercially available sulfobenzoic anhydride (XVI) may be contacted with methyl- (or ethyl)lithium in an anhydrous aprotic solvent such as diethyl ether or THF to yield the water soluble dilithium salt XVII. This salt is not isolated but warmed in aqueous mineral acid solution such as hydrochloric acid to form the water insoluble sulfone XVIII. The product XVIII is conveniently isolated by extraction with an organic solvent such as methylene chloride or chloroform and evaporation to dryness. The sulfone product thus obtained (XVIII) can be ring opened to the sulfonic acid salt XIX upon treatment with an equivalent amount of a strong alkali metal alkoxide base such as potassium tert-butoxide in tert-butanol solution at temperatures from 20° to 100° C., preferably at the boiling point of the solvent. The salt (XIX) conveniently precipitates as it is formed and can be isolated by filtration.

Conversion of the sulfonic acid salt XIX to the sulfonyl chloride (XX) proceeds in the manner as that described above for the preparation of XV. Similarly, standard amination procedures yield the sulfonamide VB.

HETEROCYCLIC AMINE DERIVATIVES

The synthesis of heterocyclic amine derivatives (IV) has been reviewed in "The Chemistry of Heterocyclic Compounds," a series published by Interscience Publ., New York and London. 2-Aminopyrimidines are described by D. J. Brown in "The Pyrimidines," Vol. XVI of the above series. The 2-amino-1,3,5-triazines are reviewed by K. R. Huffman in "The Triazines" of this same series. The synthesis of triazines is also described by F. C. Schaefer, U.S. Pat. No. 3,154,547 and by K. R. Huffman and F. C. Schaefer, J. Org. Chem., 28, 1816 (1963). The synthesis of the bicyclic aminopyrimidines have been disclosed in Unexamined European Pat. No. 15,683 and are herein incorporated by reference.

Agriculturally suitable salts of compounds of Formula I are also useful herbicides and can be prepared by a number of ways known to the art. For example, metal salts can be made by treating compounds of Formula I with a solution of alkali or alkaline earth metal salt having a sufficiently basic anion (e.g., hydroxide, alkoxide, carbonate or hydride). Quaternary amine salts can be made by similar techniques.

Salts of compounds of Formula I can also be prepared by exchange of one cation to another. Cationic exchange can be effected by direct treatment of an aqueous solution of a salt of a compound of Formula I (e.g., alkali metal or quaternary amine salt) with a solution containing the cation to be exchanged. This method is most effective when the desired salt containing the exchanged cation is insoluble in water, e.g., a copper salt, and can be separated by filtration.

Exchange may also be effected by passing an aqueous solution of a salt of a compound of Formula I (e.g., an alkali metal or quaternary amine salt) through a column packed with a cation exchange resin containing the cation to be exchanged. In this method, the cation of the resin is exchanged for that of the original salt and the desired product is eluted from the column. This method is particularly useful when the desired salt is water soluble, e.g., a potassium, sodium or calcium salt.

Acid addition salts, useful in this invention, can be obtained by reacting a compound of Formula I with a suitable acid, e.g., p-toluenesulfonic acid, trichloroacetic acid or the like.

The compounds of this invention and their preparation are further illustrated by the following examples wherein temperatures are given in degrees centigrade and parts by weight unless indicated otherwise.

The desired product is underscored at the top of each example.

EXAMPLE 1

N-[(4,6-Dimethoxypyrimidin-2-yl)aminocarbonyl]-2-formylbenzenesulfonamide

A mixture of 3.0 g of sodium bis(2-methoxyethoxy)aluminum hydride and 0.9 g of morpholine in 25 ml of dry tetrahydrofuran was cooled to −40° C. and 1.0 g of N-[(4,6-dimethoxypyrimidin-2-yl)aminocarbonyl]-2-methoxycarbonylbenzenesulfonamide was added. The resulting clear homogeneous solution was allowed to warm to room temperature over a period of 2 hours. Dilute hydrochloric acid was added and the mixture was extracted with methylene chloride. The organic extracts were washed, dried and evaporated. The crude product, which contained the desired aldehyde, the unreacted ester and the over-reduced alcohol, was purified by means of dry column chromatography. The purified product had a m.p. of 180° C.

NMR (DMSO-$d_6$)δ: 3.95 (6H, pyrimidine OCH$_3$); 5.95 (1H, pyrimidine 5-H); 7.6–8.4 (4H, aromatic); and 10.7 (1H,

EXAMPLE 2

N-[(4,6-Dimethoxypyrimidin-2-yl)aminocarbonyl]-2-ethenylbenzenesulfonamide

To a stirred mixture of 0.02 mol of n-butyllithium in 20 ml of anhydrous tetrahydrofuran is added 3.6 g of triphenylmethylphosphonium bromide. The above solution is stirred at room temperature for 4 hours. A slurry of 3.7 g of N-[(4,6-dimethoxypyrimidin-2-yl)aminocarbonyl]-2-formylbenzenesulfonamide in 30 ml of dry tetrahydrofuran is then added dropwise. The resulting mixture is refluxed overnight and allowed to cool to room temperature. The precipitate is removed by suction filtration and washed with methylene chloride. The combined filtrates are washed with dilute hydrochloric acid, water, dried and evaporated to dryness to yield the desired product.

EXAMPLE 3

N-[(4,6-Dimethoxypyrimidin-2-yl)aminocarbonyl]-2-carboxybenzenesulfonamide

N-[(4,6-Dimethoxypyrimidin-2-yl)aminocarbonyl]-2-methoxycarbonylbenzenesulfonamide (15 g) was added to a warm solution of 7.5 g of potassium hydroxide in 7.5 ml of water and 60 ml of ethanol. The mixture was stirred at room temperature overnight and then poured into dilute hydrochloric acid. The solid was filtered, washed with water and dried to afford 12.5 g of the desired product: m.p. 155°–157° C. IR (cm$^{-1}$) 3000, 1720.

NMR(DMSO-$d_6$)δ: 3.95 (6H, pyrimidine OCH$_3$); 5.8 (1H, pyrimidine 5-H); 7.7–8.3 (4H, aromatic); and no ester OCH$_3$.

EXAMPLE 4

N-[(4,6-Dimethoxypyrimidin-2-yl)aminocarbonyl]-2-acetylbenzenesulfonamide

A methyllithium solution in ether (1.4M, 40 ml) was added to a solution of 1.0 g of N-[(4,6-dimethoxypyrimidin-2-yl)aminocarbonyl]-2-carboxybenzenesulfonamide in 50 ml of dry tetrahydrofuran at room temperature. The resulting yellow slurry was stirred for 4 hours and the dilute hydrochloric acid was added. The mixture was then extracted with methylene chloride. The organic extracts were washed, dried, and evaporated in vacuo to dryness. The crude product was purified by preparative TLC, eluted with ethyl acetate/hexane (1:1), m.p. 126°–128° C.

EXAMPLE 5

N-[(4,6-Dimethoxypyrimidin-2-yl)aminocarbonyl]-2-isopropenylbenzenesulfonamide to a stirred mixture of 0.02 mol of n-butyllithium in 20 ml of anhydrous tetrahydrofuran is added 3.6 g of triphenylmethylphosphonium bromide. The above solution is stirred at room temperature for 4 hours. A slurry of 3.8 g of N-[(4,6-dimethoxypyrimidin-2-yl)aminocarbonyl]-2-acetylbenzenesulfonamide in 30 ml of dry tetrahydrofuran is then added dropwise. The resulting mixture is refluxed overnight and allowed to cool to room temperature. The precipitate is removed by suction filtration and washed with methylene chloride. The combined filtrates are then washed with diluted hydrochloric acid, water, dried and evaporated to dryness to yield the desired product.

EXAMPLE 6

N-[(4,6-Dichloro-1,3,5-triazin-2-yl)aminocarbonyl]-2-ethenylbenzenesulfonamide

A solution of 4,6-dichloro-1,3,5-triazin-2-yl isocyanate (0.87 g, 4.5 mmol) in acetonitrile (9 ml) is contacted with 2-ethenylbenzenesulfonamide (0.83 g, 4.5 mmol) and stirred for 16 hours. The mixture is then evaporated under reduced pressure to yield the title compound which is used directly in subsequent reactions.

EXAMPLE 7

N-[(4,6-Dimethoxy-1,3,5-triazin-2-yl)aminocarbonyl]-2-ethenylbenzenesulfonamide

The crude 2-ethenyl-N-[(4,6-dichloro-1,3,5-triazin-2-yl)aminocarbonyl]benzenesulfonamide of Example 6 is contacted with methanol (10 ml) and then with a solution of sodium methoxide (14 mmol) in methanol. The mixture is then stirred at room temperature for 1.5 hours and evaporated to dryness. Subsequently, the residue is taken up in water, filtered to remove unwanted solids, and acidified to precipitate the product. The crystalline product obtained can be purified by chromatography on silica gel or recrystallization to yield the title compound.

EXAMPLE 8

2-(1-Cyclopentenyl)benzenesulfonamide

A mixture of benzenesulfonic acid lithium salt (32.8 g, 0.20 mmol) and 500 ml THF was stirred in an ice bath while 138 ml (0.22 mol) of n-butyllithium solution (1.6M in hexane) was added. After stirring at room temperature for 1 hour the mixture was recooled to 0° and cyclopentanone (16.8 g, 0.20 mmol) was added dropwise; the reaction mixture was allowed to warm to ambient temperature and stirred for 24 hours. The precipitated product was collected by filtration and dried in a vacuum oven to yield 39.8 g of 2-(1-hydroxycyclopent-1-yl)benzenesulfonic acid dilithium salt.

This dilithium salt (33.1 g) was contacted with 400 ml of thionyl chloride plus 10 ml of N,N-dimethylformamide in an ice bath. After stirring for 1 hour in the ice bath the mixture was warmed to room temperature and filtered to remove inorganic by-products. The thionyl chloride was then stripped under reduced pressure to yield crude 2-(1-cyclopentenyl)benzenesulfonyl chloride which was used directly.

The sulfonyl chloride was dissolved in THF (500 ml) and concentrated ammonium hydroxide was added with external cooling at 0°–10° until the exotherm was no longer observed. The mixture was stirred at 0° for 1 hour then diluted with water and acidified to pH=3 with concentrated hydrochloric acid and extracted with methylene chloride. The extract was dried (Na$_2$SO$_4$), evaporated and triturated with chlorobutane to remove insoluble by-products by filtration. The residue from the chlorobutane filtrate was chromatographed on silica gel in 25% ethyl acetate in hexanes then crystallized from benzene to yield 5.7 g of a white powder, m.p. 112°–113° C.

NMR (CDCl$_3$)δ: 2.0 (2H, methylene); 2.3–2.9 (4H, methylenes); 6.0 (1H, olefinic); 7.3–7.6 (3H, aromatic); 8.0 (1H, aromatic); 5.1 (2H, sulfonamide);

EXAMPLE 9

2-(1-Cyclopentenyl)benzenesulfonyl Isocyanate

A solution of 2.5 g of 2-(1-cyclopentenyl)benzenesulfonamide in 20 ml of xylenes was contacted with 1.4 g of n-butylisocyanate and a trace amount (ca. 20 mg) of DABCO then heated to reflux of 139°. Liquified phosgene (1.2 ml) was then added thereby reducing the temperature and reflux continued until the boiling point of the mixture stopped rising towards the original 139° (ca. 15 min. required), which indicated a complete reaction. The solution was then evaporated under reduced pressure to yield an oil. The infrared spectrum exhibited the characteristic 2220 cm$^{-1}$ band indicating the presence of the title compound which was used directly.

EXAMPLE 10

2-(1-Cyclopentenyl)-N-[(4-methoxy-6-methylpyrimidin-2-yl)aminocarbonyl]benzenesulfonamide A mixture of 2-amino-4-methoxy-6-methylpyrimidine (0.45 g, 3.2 mmol), methylene chloride and DABCO (ca. 10 mg) was contacted with 2-(1-cyclopentenyl)benzenesulfonyl isocyanate in methylene chloride solution at ambient temperature. After approximately 20 minutes the product crystallized from the reaction mixture and was collected by filtration and rinsed with ether. In this manner, 0.35 g of product was obtained, m.p. 235°–236°. The infrared spectrum exhibited a carbonyl absorption at 1710 cm$^{-1}$ indicating the title compound.

EXAMPLE 11

3,3-Dimethyl-3H-1,2-benzoxathiole, 1,1-Dioxide

To a suspension of o-sulfobenzoic acid cyclic anhydride (Aldrich Chem. Co.) (55 g, 0.30 mmol) in ether (300 ml) was added a solution of methyllithium in ether (600 ml, 0.72 mmol) dropwise at a controlled rate to maintain a constant reflux. After addition was complete the mixture was refluxed for an additional 30 minutes then poured into a mixture of 400 g ice and 30 ml concentrated hydrochloric acid. The ether layer was separated and the aqueous phase was heated on a steam bath for approximately 1 hour then the solid which had formed was extracted with methylene chloride and evaporated to dryness. The solid product which was obtained (6.0 g) had a m.p. of 98°–100°.

NMR (DMSO-d$_6$)δ: 1.78 (6H, dimethyl); 7.4–8.0 (4H, aromatic).

EXAMPLE 12

Potassium 2-(1-methylethenyl)benzenesulfonate

Potassium tert-butoxide (1.0 g, 9.3 mmol) was dissolved in 20 ml of tert-butanol at 60°. This solution was mixed with 3,3-dimethyl-1,2-benzoxathiole, 1,1-dioxide (1.2 g, 6.3 mmol) and heated to reflux for 3 hours during which time the mixture became homogeneous; subsequently, a precipitate formed. The resulting yellow solid was then collected by filtration and rinsed with methylene chloride to yield 1.4 g of the title compound, m.p. >300°, of about 90% purity.

NMR (DMSO-d$_6$)δ: 2.10 (3H, methyl); 4.72 (1H, olefinic); 4.93 (1H, olefinic); 7.0–7.9 (4H, aromatic).

EXAMPLE 13

2-(1-Methylethenyl)benzenesulfonyl Chloride

A mixture of potassium 2-(1-methylethenyl)benzenesulfonate (7.8 g, 0.33 mmol) and 30 ml of thionyl chloride was contacted with 1.5 ml of N,N-dimethylformamide at 0°. The mixture was allowed to warm to room temperature over 45 minutes then evaporated in vacuo. Water and ether were added and the aqueous phase extracted with several portions of ether. The combined ether layers were washed with saturated sodium chloride solution, dried and evaporated under reduced pressure to yield the title compound as an oil.

NMR (CDCl$_3$)δ: 2.20 (3H, methyl); 5.02 (1H, olefinic); 5.30 (1H, olefinic); 7.3–8.0 (3H, aromatic); 8.2 (1H, aromatic).

EXAMPLE 14

2-(1-Methylethenyl)benzenesulfonamide

A solution of anhydrous ammonia (1 ml, 40 mmol) in ether (25 ml) was cooled to 0° and to this was added 2-(1-methylethenyl)benzenesulfonyl chloride of Example 13 (2.9 g, 13 mmol). After stirring for 2 hours at 0° to 5° the ammonium chloride was removed by filtration of the filtrate concentrated to an oil which crystallized on standing to give 2.6 g of the title compound, m.p. 76°–85°.

NMR (CDCl$_3$)δ: 2.18 (3H, methyl); 5.00 (1H, olefinic); 5.26 (1H, olefinic); 5.20 (2H, sulfonamide); 7.1–7.8 (3H, aromatic); 8.03 (1H, aromatic 6-H).

EXAMPLE 15

2-(1-Methylethenyl)benzenesulfonyl Isocyanate

To a refluxing mixture of 2-(1-methylethenyl)benzenesulfonamide (2.6 g, 12 mmol) and n-butylisocyanate (1.4 g, 14 mmol) in 20 ml xylenes plus a trace of DABCO (ca. 20 mg) was added liquified phosgene (1.2 ml, 16 mmol) dropwise at 139°. Refluxing was continued for 2 hours, and the solvent was removed in vacuo to give an oil. The infrared spectrum of the oil product exhibited a band at 2220 cm$^{-1}$ indicating the title compound which was stored as a solution in methylene chloride.

EXAMPLE 16

N-[(4,6-Dimethylpyrimidin-2-yl)aminocarbonyl-2-(1-methylethenyl)benzenesulfonamide A solution of 2-(1-methylethenyl)benzenesulfonyl isocyanate in methylene chloride (0.9 g, 4 mmol active ingredient) was added via syringe to a nitrogen purged flask containing a 2-amino-4,6-dimethylpyrimidine and a trace (ca. 10 mg) of DABCO. The mixture was heated to reflux for 3 hours then stirred at room temperature overnight. Evaporation of the mixture left a semi-solid residue that was triturated with ether and filtered. In this manner 0.95 g of the title compound was obtained, m.p. 177°–183°.

NMR (DMSO-$_6$)δ: 2.03 (3H, methyl); 2.40 (6H, dimethyl); 5.15 (1H, olefinic); 4.80 (1H, olefinic); 7.05 (1H, pyrimidine-5H); 7.1–7.8 (3H, aromatic); 8.13 (1H, aromatic-6H); 10.5 (1H, urea H).

Using the procedure of Examples 1 through 16 and the appropriate reactants and methods described therein, the compounds of Tables I through V may be prepared.

TABLE Ia

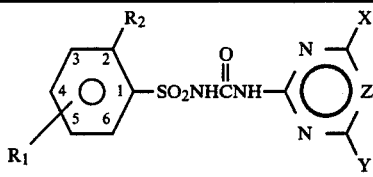

| R$_2$ | R$_1$ | X | Y | Z | m.p. |
|---|---|---|---|---|---|
| CH=CH$_2$ | H | OCH$_3$ | OCH$_3$ | CH | |
| CH=CH$_2$ | H | OCH$_3$ | CH$_3$ | CH | |
| CH=CH$_2$ | H | CH$_3$ | CH$_3$ | CH | |
| CH=CH$_2$ | H | OCH$_3$ | OCH$_3$ | N | |
| CH=CH$_2$ | H | OCH$_3$ | CH$_3$ | N | |
| CH=CH$_2$ | H | CH$_3$ | CH$_3$ | N | |
| C(CH$_3$)=CH$_2$ | H | OCH$_3$ | CH$_3$ | N | 165–167° |
| C(CH$_3$)=CH$_2$ | H | OCH$_3$ | OCH$_3$ | N | 160–165° |
| C(CH$_3$)=CH$_2$ | H | CH$_3$ | CH$_3$ | N | |
| C(CH$_3$)=CH$_2$ | H | CH$_3$ | CH$_3$ | CH | 177–183° |
| C(CH$_3$)=CH$_2$ | H | CH$_3$ | OCH$_3$ | CH | 184–190° |
| C(CH$_3$)=CH$_2$ | H | OCH$_3$ | OCH$_3$ | CH | 201–211° |
| CH=CH$_2$ | 5-Cl | CH$_2$OCH$_3$ | OCH$_3$ | CH | |
| CH=CHCH$_3$ | H | CH$_3$ | OC$_2$H$_5$ | N | |
| CH=CHC$_2$H$_5$ | 6-Br | OCH$_2$CF$_3$ | CH$_3$ | CH | |
| CH=CH(CH$_2$)$_2$CH$_3$ | 4-F | H | OCH$_3$ | CH | |
| CH=CHCH(CH$_3$)$_2$ | 5-NO$_2$ | Cl | CH$_3$ | CH | |
| CH=C(CH$_3$)$_2$ | H | CH$_3$ | OCH$_3$ | N | |
| CH=C(CH$_3$)C$_2$H$_5$ | 5-CF$_3$ | CH$_3$ | OCH$_3$ | CCl | |
| CCl=CCl$_2$ | H | CH$_3$ | CH$_3$ | CH | |
| CH=CCl$_2$ | H | CH$_3$ | OCH$_3$ | CH | |
| CCl=CHCl | H | CH$_3$ | OCH$_3$ | N | |
| CH=CHCl | 5-C(CH$_3$)$_3$ | CH$_3$ | NH$_2$ | N | |
| CH=CH—CCl$_3$ | 6-CH$_3$ | CH$_3$ | NHCH$_3$ | N | |
| CH=CCl—CHCl$_2$ | 3-OCH$_3$ | CH$_3$ | N(CH$_3$)$_2$ | CH | |
| CCl=CClCH$_2$Cl | 5-OCF$_3$ | OCH$_2$CF$_3$ | CH$_3$ | CH | |
| C(CH$_3$)=CHC$_2$H$_5$ | H | OCH$_3$ | OCH$_3$ | CBr | |
| C(CH$_3$)=C(CH$_3$)$_2$ | H | OCH$_3$ | CH$_3$ | CCN | |
| C(CH$_3$)=CHCH$_3$ | 5-OC$_3$H$_7$ | CH$_3$ | CH$_3$ | OCH$_3$ | |
| C(C$_2$H$_5$)=CH$_2$ | H | OCH$_3$ | CH$_3$ | OC$_2$H$_5$ | |
| C(C$_2$H$_5$)=CHCH$_3$ | H | CH$_3$ | OCH$_3$ | OCH$_2$CH$_2$Cl | |
| C(C$_2$H$_5$)=CHCH$_3$ | 6-OC$_2$H$_5$ | OCH$_3$ | OCH$_3$ | OCH$_2$CH=CH$_2$ | |
|  | H | CH$_3$ | CH$_3$ | CH | 206–208° |

TABLE Ia-continued

[Structure: benzene ring with R₂ at position 2, R₁ at position 5, and -SO₂NHCNH- (with C=O) connecting to a heterocyclic ring containing N, X, Z, Y]

| R₂ | R₁ | X | Y | Z | m.p. |
|---|---|---|---|---|---|
| cyclopentenyl | H | CH₃ | OCH₃ | CH | 235–236° |
| cyclopentenyl | H | OCH₃ | OCH₃ | CH | 182–185° |
| cyclopentenyl | H | CH₃ | CH₃ | N | |
| cyclopentenyl | H | OCH₃ | CH₃ | N | >250° |
| cyclopentenyl | H | OCH₃ | OCH₃ | N | 162–165° |
| cyclohexenyl | H | CH₃ | OCH₃ | CH | |
| cyclohexenyl | H | CH₃ | CH₃ | CH | |
| cyclohexenyl | H | OCH₃ | OCH₃ | CH | |
| cyclohexenyl | H | CH₃ | CH₃ | N | |
| cyclohexenyl | H | CH₃ | OCH₃ | N | |
| cyclohexenyl | H | OCH₃ | OCH₃ | N | |
| | H | CH₃ | CH₃ | CH | |

TABLE Ia-continued

| R₂ | R₁ | X | Y | Z | m.p. |
|---|---|---|---|---|---|
| 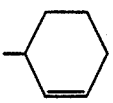 | H | CH₃ | OCH₃ | CH | |
| 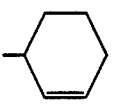 | H | CH₃ | OCH₃ | N | |
| 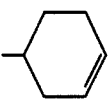 | H | OCH₃ | OCH₃ | N | |
| 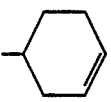 | H | OCH₃ | OCH₃ | CH | |
| (cyclohexenyl) | H | OCH₃ | CH₃ | CH | |
| C(CH₃)=CH₂ | H | Cl | CH₃ | N | |

TABLE Ib

| R₂ | R₁ | X | Y | Z | m.p. |
|---|---|---|---|---|---|
| CH=CH₂ | H | OCH₃ | OCH₃ | CH | |
| CH=CH₂ | H | OCH₃ | CH₃ | CH | |
| CH=CH₂ | H | CH₃ | CH₃ | CH | |
| CH=CH₂ | H | OCH₃ | OCH₃ | N | |
| CH=CH₂ | H | OCH₃ | CH₃ | N | |
| CH=CH₂ | H | CH₃ | CH₃ | N | |
| C(CH₃)=CH₂ | H | OCH₃ | CH₃ | N | |
| C(CH₃)=CH₂ | H | OCH₃ | OCH₃ | N | |
| C(CH₃)=CH₂ | H | CH₃ | CH₃ | N | |
| C(CH₃)=CH₂ | H | CH₃ | CH₃ | CH | |
| C(CH₃)=CH₂ | H | CH₃ | OCH₃ | CH | |
| C(CH₃)=CH₂ | H | OCH₃ | OCH₃ | CH | |
| CH=CH₂ | 5-Cl | CH₂OCH₃ | OCH₃ | CH | |
| CH=CHCH₃ | H | CH₃ | OC₂H₅ | N | |
| CH=CHC₂H₅ | 6-Br | OCH₂CF₃ | CH₃ | CH | |
| CH=CH(CH₂)₂CH₃ | 4-F | H | OCH₃ | CH | |
| CH=CHCH(CH₃)₂ | 5-NO₂ | Cl | CH₃ | CH | |
| CH=C(CH₃)₂ | H | CH₃ | OCH₃ | N | |
| CH=C(CH₃)C₂H₅ | 5-CF₃ | CH₃ | OCH₃ | CCl | |
| CCl=CCl₂ | H | CH₃ | CH₃ | CH | |
| CCl=CCl₂ | H | CH₃ | OCH₃ | CH | |
| CCl=CHCl | H | CH₃ | OCH₃ | N | |
| CH=CHCl | 5-C(CH₃)₃ | CH₃ | NH₂ | N | |
| CH=CH—CCl₃ | 6-CH₃ | CH₃ | NHCH₃ | N | |
| CH=CCl—CHCl₂ | 3-OCH₃ | CH₃ | N(CH₃)₂ | CH | |
| CCl=CClCH₂Cl | 5-OCF₃ | OCH₂CF₃ | CH₃ | CH | |

TABLE Ib-continued

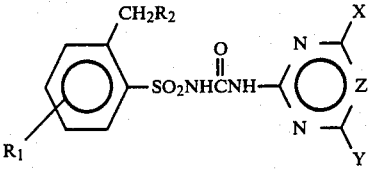

| $R_2$ | $R_1$ | X | Y | Z | m.p. |
|---|---|---|---|---|---|
| C(CH$_3$)=CHC$_2$H$_5$ | H | OCH$_3$ | OCH$_3$ | CBr | |
| C(CH$_3$)=C(CH$_3$)$_2$ | H | OCH$_3$ | CH$_3$ | CCN | |
| C(CH$_3$)=CHCH$_3$ | 5-OC$_3$H$_7$ | CH$_3$ | CH$_3$ | OCH$_3$ | |
| C(C$_2$H$_5$)=CH$_2$ | H | OCH$_3$ | CH$_3$ | OC$_2$H$_5$ | |
| C(C$_2$H$_5$)=CHCH$_3$ | H | CH$_3$ | OCH$_3$ | OCH$_2$CH$_2$Cl | |
| C(C$_2$H$_5$)=CHCH$_3$ | 6-OC$_2$H$_5$ | OCH$_3$ | OCH$_3$ | OCH$_2$CH=CH$_2$ | |
|  | H | CH$_3$ | CH$_3$ | CH | |
|  | H | CH$_3$ | OCH$_3$ | CH | |
|  | H | OCH$_3$ | OCH$_3$ | CH | |
|  | H | CH$_3$ | CH$_3$ | N | |
|  | H | OCH$_3$ | CH$_3$ | N | |
|  | H | OCH$_3$ | OCH$_3$ | N | |
|  | H | CH$_3$ | OCH$_3$ | CH | |
|  | H | CH$_3$ | CH$_3$ | CH | |
|  | H | OCH$_3$ | OCH$_3$ | CH | |
|  | H | CH$_3$ | CH$_3$ | N | |
|  | H | CH$_3$ | OCH$_3$ | N | |

TABLE Ib-continued

[Structure: benzene ring with CH₂R₂ (ortho), R₁ (para), and SO₂NHCNH-(heterocycle) with O double bond; heterocycle has N, X, Z, N, Y substituents]

| R₂ | R₁ | X | Y | Z | m.p. |
|---|---|---|---|---|---|
| [cyclohexenyl] | H | OCH₃ | OCH₃ | N | |
| [cyclopentenyl] | H | CH₃ | CH₃ | CH | |
| [cyclopentenyl] | H | CH₃ | OCH₃ | CH | |
| [cyclohexenyl] | H | CH₃ | OCH₃ | N | |
| [cyclohexenyl] | H | OCH₃ | OCH₃ | N | |
| [cyclohexenyl] | H | OCH₃ | OCH₃ | CH | |
| [cyclohexenyl] | H | OCH₃ | CH₃ | CH | |
| C(CH₃)=CH₂ | H | Cl | CH₃ | N | |

TABLE Ic

[Structure: benzene ring with CH₃-CHR₂ substituent, R₁, and SO₂NHCNH-(heterocycle) with O double bond]

| R₂ | R₁ | X | Y | Z | m.p. |
|---|---|---|---|---|---|
| CH=CH₂ | H | OCH₃ | OCH₃ | CH | |
| CH=CH₂ | H | OCH₃ | CH₃ | CH | |
| CH=CH₂ | H | CH₃ | CH₃ | CH | |
| CH=CH₂ | H | OCH₃ | OCH₃ | N | |
| CH=CH₂ | H | OCH₃ | CH₃ | N | |
| CH=CH₂ | H | CH₃ | CH₃ | N | |
| C(CH₃)=CH₂ | H | OCH₃ | CH₃ | N | |
| C(CH₃)=CH₂ | H | OCH₃ | OCH₃ | N | |
| C(CH₃)=CH₂ | H | CH₃ | CH₃ | N | |
| C(CH₃)=CH₂ | H | CH₃ | CH₃ | CH | |
| C(CH₃)=CH₂ | H | CH₃ | OCH₃ | CH | |
| C(CH₃)=CH₂ | H | OCH₃ | OCH₃ | CH | |

TABLE Ic-continued

| R2 | R1 | X | Y | Z | m.p. |
|---|---|---|---|---|---|
| CH=CH$_2$ | 5-Cl | CH$_2$OCH$_3$ | OCH$_3$ | CH | |
| CH=CHCH$_3$ | H | CH$_3$ | OC$_2$H$_5$ | N | |
| CH=CHC$_2$H$_5$ | 6-Br | OCH$_2$CF$_3$ | CH$_3$ | CH | |
| CH=CH(CH$_2$)$_2$CH$_3$ | 4-F | H | OCH$_3$ | CH | |
| CH=CHCH(CH$_3$)$_2$ | 5-NO$_2$ | Cl | CH$_3$ | CH | |
| CH=C(CH$_3$)$_2$ | H | CH$_3$ | OCH$_3$ | N | |
| CH=C(CH$_3$)C$_2$H$_5$ | 5-CF$_3$ | CH$_3$ | OCH$_3$ | CCl | |
| CCl=CCl$_2$ | H | CH$_3$ | CH$_3$ | CH | |
| CH=CCl$_2$ | H | CH$_3$ | OCH$_3$ | CH | |
| CCl=CHCl | H | CH$_3$ | OCH$_3$ | N | |
| CH=CHCl | 5-C(CH$_3$)$_3$ | CH$_3$ | NH$_2$ | N | |
| CH=CH—CCl$_3$ | 6-CH$_3$ | CH$_3$ | NHCH$_3$ | N | |
| CH=CCl—CHCl$_2$ | 3-OCH$_3$ | CH$_3$ | N(CH$_3$)$_2$ | CH | |
| CCl=CClCH$_2$Cl | 5-OCF$_3$ | OCH$_2$CF$_3$ | CH$_3$ | CH | |
| C(CH$_3$)=CHC$_2$H$_5$ | H | OCH$_3$ | OCH$_3$ | CBr | |
| C(CH$_3$)=C(CH$_3$)$_2$ | H | OCH$_3$ | CH$_3$ | CCN | |
| C(CH$_3$)=CHCH$_3$ | 5-OC$_3$H$_7$ | CH$_3$ | CH$_3$ | OCH$_3$ | |
| C(C$_2$H$_5$)=CH$_2$ | H | OCH$_3$ | CH$_3$ | OC$_2$H$_5$ | |
| C(C$_2$H$_5$)=CHCH$_3$ | H | CH$_3$ | OCH$_3$ | OCH$_2$CH$_2$Cl | |
| C(C$_2$H$_5$)=CHCH$_3$ | 6-OC$_2$H$_5$ | OCH$_3$ | OCH$_3$ | OCH$_2$CH=CH$_2$ | |
|  | H | CH$_3$ | CH$_3$ | CH | |
|  | H | CH$_3$ | OCH$_3$ | CH | |
|  | H | OCH$_3$ | OCH$_3$ | CH | |
|  | H | CH$_3$ | CH$_3$ | N | |
|  | H | OCH$_3$ | CH$_3$ | N | |
|  | H | OCH$_3$ | OCH$_3$ | N | |
|  | H | CH$_3$ | OCH$_3$ | CH | |
|  | H | CH$_3$ | CH$_3$ | CH | |

TABLE Ic-continued

Structure:
2-(CH(CH₃)R₂)-4-R₁-C₆H₃-SO₂NHC(O)NH-[pyrimidine/triazine with X, Y, Z]

| R₂ | R₁ | X | Y | Z | m.p. |
|---|---|---|---|---|---|
| cyclohexenyl | H | OCH₃ | OCH₃ | CH | |
| cyclohexenyl | H | CH₃ | CH₃ | N | |
| cyclohexenyl | H | CH₃ | OCH₃ | N | |
| cyclohexenyl | H | OCH₃ | OCH₃ | N | |
| cyclopentenyl | H | CH₃ | CH₃ | CH | |
| cyclopentenyl | H | CH₃ | OCH₃ | CH | |
| cyclohexenyl | H | CH₃ | OCH₃ | N | |
| cyclohexenyl | H | OCH₃ | OCH₃ | N | |
| cyclohexenyl | H | OCH₃ | OCH₃ | CH | |
| cyclohexenyl | H | OCH₃ | CH₃ | CH | |
| C(CH₃)=CH₂ | H | Cl | CH₃ | N | |

TABLE Id

Structure: Benzene ring with C(CH₃)₂R₂ ortho to SO₂NHCNH-C(=O)-pyrimidine/triazine (with X, Y, Z substituents), R₁ on benzene.

| R₂ | R₁ | X | Y | Z | m.p. |
|---|---|---|---|---|---|
| CH=CH₂ | H | OCH₃ | OCH₃ | CH | |
| CH=CH₂ | H | OCH₃ | CH₃ | CH | |
| CH=CH₂ | H | CH₃ | CH₃ | CH | |
| CH=CH₂ | H | OCH₃ | OCH₃ | N | |
| CH=CH₂ | H | OCH₃ | CH₃ | N | |
| CH=CH₂ | H | CH₃ | CH₃ | N | |
| C(CH₃)=CH₂ | H | OCH₃ | CH₃ | N | |
| C(CH₃)=CH₂ | H | OCH₃ | OCH₃ | N | |
| C(CH₃)=CH₂ | H | CH₃ | CH₃ | N | |
| C(CH₃)=CH₂ | H | CH₃ | CH₃ | CH | |
| C(CH₃)=CH₂ | H | CH₃ | OCH₃ | CH | |
| C(CH₃)=CH₂ | H | OCH₃ | OCH₃ | CH | |
| CH=CH₂ | 5-Cl | CH₂OCH₃ | OCH₃ | CH | |
| CH=CHCH₃ | H | CH₃ | OC₂H₅ | N | |
| CH=CHC₂H₅ | 6-Br | OCH₂CF₃ | CH₃ | CH | |
| CH=CH(CH₂)₂CH₃ | 4-F | H | OCH₃ | CH | |
| CH=CHCH(CH₃)₂ | 5-NO₂ | Cl | CH₃ | CH | |
| CH=C(CH₃)₂ | H | CH₃ | OCH₃ | N | |
| CH=C(CH₃)C₂H₅ | 5-CF₃ | CH₃ | OCH₃ | CCl | |
| CCl=CCl₂ | H | CH₃ | CH₃ | CH | |
| CH=CCl₂ | H | CH₃ | OCH₃ | CH | |
| CCl=CHCl | H | CH₃ | OCH₃ | N | |
| CH=CHCl | 5-C(CH₃)₃ | CH₃ | NH₂ | N | |
| CH=CH—CCl₃ | 6-CH₃ | CH₃ | NHCH₃ | N | |
| CH=CCl—CHCl₂ | 3-OCH₃ | CH₃ | N(CH₃)₂ | CH | |
| CCl=CClCH₂Cl | 5-OCF₃ | OCH₂CF₃ | CH₃ | CH | |
| C(CH₃)=CHC₂H₅ | H | OCH₃ | OCH₃ | CBr | |
| C(CH₃)=C(CH₃)₂ | H | OCH₃ | CH₃ | OCN | |
| C(CH₃)=CHCH₃ | 5-OC₃H₇ | CH₃ | CH₃ | OCH₃ | |
| C(C₂H₅=CH₂ | H | OCH₃ | CH₃ | OC₂H₅ | |
| C(C₂H₅)=CHCH₃ | H | CH₃ | OCH₃ | OCH₂CH₂Cl | |
| C(C₂H₅)=CHCH₃ | 6-OC₂H₅ | OCH₃ | OCH₃ | OCH₂CH=CH₂ | |
| cyclopentenyl | H | CH₃ | CH₃ | CH | |
| cyclopentenyl | H | CH₃ | OCH₃ | CH | |
| cyclopentenyl | H | OCH₃ | OCH₃ | CH | |
| cyclopentenyl | H | CH₃ | CH₃ | N | |
| cyclopentenyl | H | OCH₃ | CH₃ | N | |
| cyclopentenyl | H | OCH₃ | OCH₃ | N | |

TABLE Id-continued
![structure](header structure: C(CH3)2R2 and R1 substituted phenyl-SO2NHC(O)NH-pyrimidine with X, Y, Z substituents)
| R2 | R1 | X | Y | Z | m.p. |
|---|---|---|---|---|---|
| 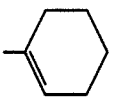 | H | CH3 | OCH3 | CH | |
| 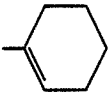 | H | CH3 | CH3 | CH | |
| 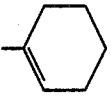 | H | OCH3 | OCH3 | CH | |
| 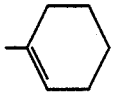 | H | CH3 | CH3 | N | |
| 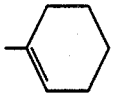 | H | CH3 | OCH3 | N | |
| 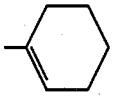 | H | OCH3 | OCH3 | N | |
| 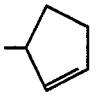 | H | CH3 | CH3 | CH | |
| 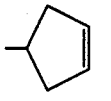 | H | CH3 | OCH3 | CH | |
| 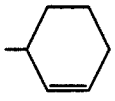 | H | CH3 | OCH3 | N | |
|  | H | OCH3 | OCH3 | N | |
| 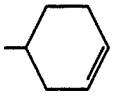 | H | OCH3 | OCH3 | CH | |
| 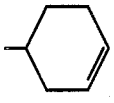 | H | OCH3 | CH3 | CH | |

TABLE Id-continued

Structure: phenyl with C(CH₃)₂R₂ ortho, R₁ para, SO₂NHC(O)NH linked to pyrimidine with X, Y, Z substituents

| R₂ | R₁ | X | Y | Z | m.p. |
|---|---|---|---|---|---|
| C(CH₃)=CH₂ | H | Cl | CH₃ | N | |

TABLE IIa

Structure: phenyl with R₂ ortho, R₁ para, SO₂NHC(O)NH linked to fused pyrimidine with Y₁ and Q substituents

| R₂ | R₁ | Y₁ | Q | m.p. |
|---|---|---|---|---|
| CH=CH₂ | H | CH₃ | CH₂ | |
| CH=CH₂ | H | OCH₃ | CH₂ | |
| C(CH₃)=CH₂ | H | CH₃ | CH₂ | |
| C(CH₃)=CH₂ | H | OCH₃ | CH₂ | |
| CH=CHCH₃ | H | CH₃ | CH₂ | |
| CH=CHCH₃ | H | OCH₃ | CH₂ | |
| CH=C(CH₃)₂ | H | CH₃ | CH₂ | |
| CH=C(CH₃)₂ | H | OCH₃ | CH₂ | |
| CH=CHC₂H₅ | H | H | CH₂ | |
| CH=CHC₂H₅ | 5-Cl | Cl | CH₂ | |
| CH=C(CH₃)C₂H₅ | H | CH₃ | CH₂ | |
| C(CH₃)=CHCH₃ | H | OCH₃ | CH₂ | |
| C(CH₃)=C(CH₃)₂ | H | CH₃ | CH₂ | |
| 1-cyclopentenyl | H | OCH₃ | CH₂ | |
| 1-cyclopentenyl | H | CH₃ | CH₂ | |
| 1-cyclohexenyl | H | OCH₃ | CH₂ | |
| 1-cyclohexenyl | H | H | CH₂ | |
| C(CH₃)=CH₂ + 1-cyclohexenyl | H | Cl | CH₂ | |
| 1-cyclohexenyl | 5-CF₃ | CH₃ | CH₂ | |
| 3-cyclohexenyl | H | CH₃ | CH₂ | |
| CH=CH₂ | H | CH₃ | O | |
| CH=CH₂ | H | OCH₃ | O | |
| C(CH₃)=CH₂ | H | CH₃ | O | |
| C(CH₃)=CH₂ | H | OCH₃ | O | |
| CH=CHCH₃ | H | CH₃ | O | |
| CH=CHCH₃ | H | OCH₃ | O | |
| CH=C(CH₃)₂ | H | CH₃ | O | |
| CH=C(CH₃)₂ | H | OCH₃ | O | |
| CH=CHC₂H₅ | H | H | O | |
| CH=CHC₂H₅ | 5-Cl | Cl | O | |
| CH=C(CH₃)C₂H₅ | H | CH₃ | O | |
| C(CH₃)=CHCH₃ | H | OCH₃ | O | |
| C(CH₃)=C(CH₃)₂ | H | CH₃ | O | |
| 1-cyclopentenyl | H | OCH₃ | O | |
| 1-cyclopentenyl | H | CH₃ | O | |
| 1-cyclohexenyl | H | OCH₃ | O | |
| 1-cyclohexenyl | H | H | O | |
| C(CH₃)=CH₂ + 1-cyclohexenyl | H | Cl | O | |
| 1-cyclohexenyl | 5-CF₃ | CH₃ | O | |
| 3-cyclohexenyl | H | CH₃ | O | |

TABLE IIb

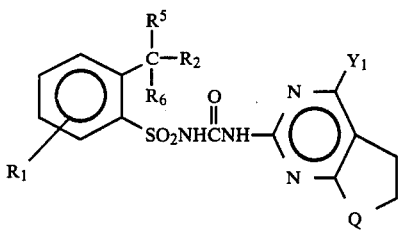

| R2 | R1 | R5 | R6 | Y1 | Q |
|---|---|---|---|---|---|
| CH=CH2 | H | H | H | CH3 | CH2 |
| CH=CH2 | H | H | CH3 | OCH3 | CH2 |
| C(CH3)=CH2 | H | CH3 | CH3 | CH3 | CH2 |
| C(CH3)=CH2 | H | H | H | OCH3 | CH2 |
| CH=CHCH3 | H | H | CH3 | CH3 | CH2 |
| CH=CHCH3 | H | H | OCH3 | OCH3 | CH2 |
| CH=C(CH3)2 | H | H | H | CH3 | CH2 |
| CH=C(CH3)2 | H | CH3 | CH3 | OCH3 | CH2 |
| CH=CHC2H5 | 6-F | H | CH3 | CH3 | CH2 |
| CH=CHC2H5 | H | H | CH3 | OCH3 | CH2 |
| CH=C(CH3)C2H5 | H | H | H | CH3 | CH2 |
| C(CH3)=CHCH3 | H | H | H | OCH3 | CH2 |
| C(CH3)=(CH3)2 | H | H | H | CH3 | CH2 |
| cyclopentenyl | H | H | CH3 | OCH3 | CH2 |
| cyclopentenyl | H | H | CH3 | Cl | CH2 |
| cyclohexenyl | H | CH3 | H | CH3 | CH2 |
| cyclohexenyl | H | H | H | H | CH2 |
| C(CH3)CH=CH2 | H | H | H | OCH3 | CH2 |
| cyclohexenyl | 5-NO2 | H | H | CH3 | CH2 |
| cyclohexenyl | H | H | H | CH3 | CH2 |
| CH=CH2 | H | H | H | CH3 | O |
| CH=CH2 | H | H | CH3 | OCH3 | O |
| C(CH3)=CH2 | H | CH3 | CH3 | CH3 | O |
| C(CH3)=CH2 | H | H | H | OCH3 | O |
| CH=CHCH3 | H | H | CH3 | CH3 | O |
| CH=CHCH3 | H | H | CH3 | OCH3 | O |
| CH=C(CH3)2 | H | H | H | CH3 | O |
| CH=C(CH3)2 | H | CH3 | CH3 | OCH3 | O |
| CH=CHC2H5 | 6-F | H | CH3 | CH3 | O |
| CH=CHC2H5 | H | H | CH3 | OCH3 | O |
| CH=C(CH3)C2H5 | H | H | H | CH3 | O |
| C(CH3)=CHCH3 | H | H | H | OCH3 | O |
| C(CH3)=C(CH3)2 | H | H | H | CH3 | O |

TABLE IIb-continued

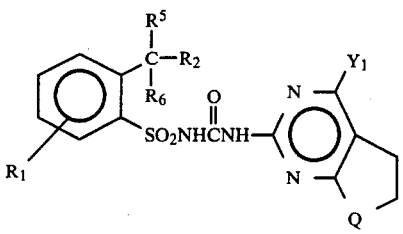

| R2 | R1 | R5 | R6 | Y1 | Q |
|---|---|---|---|---|---|
| cyclopentenyl | H | H | CH3 | OCH3 | O |
| cyclopentenyl | H | H | CH3 | Cl | O |
| cyclohexenyl | H | CH3 | H | CH3 | O |
| cyclohexenyl | H | H | H | H | O |
| C(CH3)CH=CH2 | H | H | H | OCH3 | O |
| cyclohexenyl | 5-NO2 | H | H | CH3 | O |
| cyclohexenyl | H | H | H | CH3 | O |

TABLE IIIa

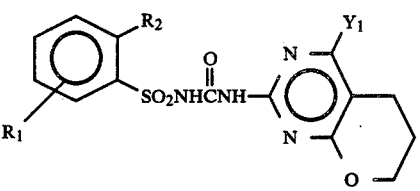

| R2 | R1 | Y1 |
|---|---|---|
| CH=CH2 | H | CH3 |
| CH=CH2 | H | OCH3 |
| C(CH3)=CH2 | H | CH3 |
| C(CH3)=CH2 | H | OCH3 |
| CH=CHCH3 | H | CH3 |
| CH=CHCH3 | H | OCH3 |
| CH=C(CH3)2 | H | CH3 |
| CH=C(CH3)2 | H | OCH3 |
| CH=CHC2H5 | H | H |
| CH=CHC2H5 | 5-Cl | Cl |
| CH=C(CH3)C2H5 | H | CH3 |
| C(CH3)=CHCH3 | H | OCH3 |
| C(CH3)=C(CH3)2 | H | CH3 |

TABLE IIIa-continued

[Structure: phenyl with $R_2$ (ortho) and $R_1$ substituents, connected via $SO_2NHCNH$ (C=O) to a fused pyrimidine-oxygen ring with $Y_1$]

| $R_2$ | $R_1$ | $Y_1$ |
|---|---|---|
| 1-cyclopentenyl | H | OCH$_3$ |
| 1-cyclopentenyl | H | CH$_3$ |
| 1-cyclohexenyl | H | OCH$_3$ |
| 1-cyclohexenyl | H | H |
| C(CH$_3$)=CH$_2$ | H | Cl |
| 1-cyclohexenyl | 5-CF$_3$ | CH$_3$ |
| 3-cyclohexenyl | H | CH$_3$ |

TABLE IIIb

[Structure: phenyl with $C(R_5)(R_2)(R_6)$ ortho and $R_1$ substituents, connected via $SO_2NHCNH$ (C=O) to a fused pyrimidine-oxygen ring with $Y_1$]

| $R_2$ | $R_1$ | $R_5$ | $R_6$ | $Y_1$ |
|---|---|---|---|---|
| CH=CH$_2$ | H | H | H | CH$_3$ |
| CH=CH$_2$ | H | H | CH$_3$ | OCH$_3$ |
| C(CH$_3$)=CH$_2$ | H | CH$_3$ | CH$_3$ | CH$_3$ |
| C(CH$_3$)=CH$_2$ | H | H | H | OCH$_3$ |
| CH=CHCH$_3$ | H | H | CH$_3$ | CH$_3$ |
| CH=CHCH$_3$ | H | H | CH$_3$ | OCH$_3$ |
| CH=C(CH$_3$)$_2$ | H | H | H | CH$_3$ |
| CH=C(CH$_3$)$_2$ | H | CH$_3$ | CH$_3$ | OCH$_3$ |
| CH=CHC$_2$H$_5$ | 6-F | H | CH$_3$ | CH$_3$ |
| CH=CHC$_2$H$_5$ | H | H | CH$_3$ | OCH$_3$ |
| CH=C(CH$_3$)C$_2$H$_5$ | H | H | H | CH$_3$ |
| C(CH$_3$)=CHCH$_3$ | H | H | H | OCH$_3$ |
| C(CH$_3$)=C(CH$_3$)$_2$ | H | H | H | CH$_3$ |

TABLE IIIb-continued

| $R_2$ | $R_1$ | $R_5$ | $R_6$ | $Y_1$ |
|---|---|---|---|---|
| 1-cyclopentenyl | H | H | CH$_3$ | OCH$_3$ |
| 1-cyclopentenyl | H | H | CH$_3$ | Cl |
| 1-cyclohexenyl | H | CH$_3$ | H | CH$_3$ |
| 1-cyclohexenyl | H | H | H | H |
| C(CH$_3$)CH=CH$_2$ | H | H | H | OCH$_3$ |
| 1-cyclohexenyl | 5-NO$_2$ | H | H | CH$_3$ |
| 3-cyclohexenyl | H | H | H | CH$_3$ |

TABLE IVa

[Structure: phenyl with $R_2$ (ortho) and $R_1$ substituents, connected via $SO_2NHCNH$ (C=O) to a triazine ring with $X_2$ and $Y_2$]

| $R_2$ | $R_1$ | $X_2$ | $Y_2$ |
|---|---|---|---|
| CH=CH$_2$ | H | CH$_3$ | CH$_3$ |
| CH=CHCH$_3$ | H | CH$_3$ | OCH$_3$ |
| C(CH$_3$)=CH$_2$ | H | OCH$_3$ | OCH$_3$ |
| C(CH$_3$)=CH$_2$ | H | CH$_3$ | CH$_3$ |
| C(CH$_3$)=CH$_2$ | H | CH$_3$ | OCH$_3$ |
| C(CH$_3$)=CH$_2$ | H | OCH$_3$ | OCH$_3$ |
| CH=CHC$_2$H$_5$ | 5-Br | CH$_3$ | CH$_3$ |
| CCl=CHCl | H | CH$_3$ | OCH$_3$ |
| C(CH$_3$)=CHC$_2$H$_5$ | H | OCH$_3$ | OCH$_3$ |
| 1-cyclopentenyl | H | OCH$_3$ | CH$_3$ |

TABLE IVa-continued

Structure: phenyl(R2 ortho, R1)-SO2NHC(O)NH-[1,2,4-triazine with X2, Y2]

| R2 | R1 | X2 | Y2 |
|---|---|---|---|
| cyclopentenyl | H | CH3 | CH3 |
| cyclopentenyl | H | OCH3 | OCH3 |
| cyclohexenyl | H | OCH3 | CH3 |
| cyclohexenyl | 3-OCH3 | CH3 | CH3 |
| cyclohexenyl | H | OCH3 | OCH3 |

TABLE IVb

Structure: phenyl with ortho -C(R5)(R2)(R6), and R1; SO2NHC(O)NH-triazine(X2,Y2)

| R2 | R1 | R5 | R6 | X2 | Y2 |
|---|---|---|---|---|---|
| CH=CH2 | H | H | H | CH3 | CH3 |
| CH=CH2 | H | CH3 | CH3 | CH3 | OCH3 |
| CH=CHCH3 | H | H | H | OCH3 | CH3 |
| CH=CHCH3 | H | H | CH3 | OCH3 | CH3 |
| C(CH3)=CH2 | H | H | H | CH3 | OCH3 |
| C(CH3)=CH2 | H | H | H | OCH3 | OCH3 |
| C(CH3)=CH2 | 5-NO2 | H | H | CH3 | CH3 |
| C(CH3)=CHCH3 | H | H | H | OCH3 | OCH3 |
| CH=CH(CH2)2CH3 | H | CH3 | H | OCH3 | CH3 |
| CH=C(CH3)2 | H | CH3 | H | CH3 | CH3 |
| CH=C(CH3)2 | H | H | H | OCH3 | CH3 |
| cyclopentenyl | 3-CH3 | H | CH3 | OCH3 | CH3 |
| cyclopentenyl | H | H | H | CH3 | CH3 |

TABLE IVb-continued

| R2 | R1 | R5 | R6 | X2 | Y2 |
|---|---|---|---|---|---|
| cyclohexenyl | 4-OCH3 | H | H | CH3 | OCH3 |
| cyclohexenyl | H | H | H | CH3 | CH3 |

TABLE Va

Structure: phenyl(R2 ortho, R1)-SO2NHC(O)NH-pyrimidine(X2, Y2)

| R2 | R1 | X2 | Y2 |
|---|---|---|---|
| CH=CH2 | H | CH3 | CH3 |
| CH=CHCH3 | H | CH3 | OCH3 |
| C(CH3)=CH2 | H | OCH3 | OCH3 |
| C(CH3)=CH2 | H | CH3 | CH3 |
| C(CH3)=CH2 | H | CH3 | OCH3 |
| C(CH3)=CH2 | H | OCH3 | OCH3 |
| CH=CHC2H5 | 5-Br | CH3 | CH3 |
| CCl=CHCl | H | CH3 | OCH3 |
| C(CH3)=CHC2H5 | H | OCH3 | OCH3 |
| cyclopentenyl | H | OCH3 | CH3 |
| cyclopentenyl | H | CH3 | CH3 |
| cyclopentenyl | H | OCH3 | OCH3 |
| cyclohexenyl | H | OCH3 | CH3 |
| cyclohexenyl | 3-OCH3 | CH3 | CH3 |

TABLE Va-continued

[Structure: benzene ring with R2 ortho, R1, SO2NHCNH-pyridine with X2, Y2, C=O]

| R2 | R1 | X2 | Y2 |
|---|---|---|---|
| cyclohexenyl | H | OCH3 | OCH3 |

TABLE Vb

[Structure: benzene ring with C(R5)(R6)-R2, R1, SO2NHCNH-pyridine with X2, Y2]

| R2 | R1 | R5 | R6 | X2 | Y2 |
|---|---|---|---|---|---|
| CH=CH2 | H | H | H | CH3 | CH3 |
| CH=CH2 | H | CH3 | CH3 | CH3 | OCH3 |
| CH=CHCH3 | H | H | H | OCH3 | CH3 |
| CH=CHCH3 | H | H | H | CH3 | OCH3 |
| C(CH3)=CH2 | H | H | H | CH3 | OCH3 |
| C(CH3)=CH2 | H | H | H | OCH3 | OCH3 |
| C(CH3)=CH2 | 5-NO2 | H | H | CH3 | CH3 |
| C(CH3)=CHCH3 | H | H | H | CH3 | OCH3 |
| CH=CH(CH2)2CH3 | H | CH3 | H | OCH3 | CH3 |
| CH=C(CH3)2 | H | CH3 | H | CH3 | CH3 |
| CH=C(CH3)2 | H | H | H | OCH3 | CH3 |
| cyclopentenyl | 3-CH3 | H | CH3 | OCH3 | CH3 |
| cyclopentenyl | H | H | H | CH3 | CH3 |
| cyclohexenyl | 4-OCH3 | H | H | CH3 | OCH3 |
| cyclohexenyl | H | H | CH3 | CH3 | CH3 |

FORMULATIONS

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE VI

| | Active Ingredient | Weight Percent* Diluent(s) | Surfactant(s) |
|---|---|---|---|
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1976, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley & Sons, Inc., New York, 1961, pp. 81–96; and J. D. Fryer and S. A. Evans, "Weed Contol Handbook", 5th Ed., Blackwell Scientific Publications, Oxford, 1968, pp. 101–103.

In the following examples, all parts are by weight unless otherwise indicated.

EXAMPLE 17

Wettable Powder

| | |
|---|---|
| 2-(1-cyclopentenyl)-N—[(4,6-dimethylpyrimidin-2-yl)aminocarbonyl]benzenesulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 18

Wettable Powder

| | |
|---|---|
| N—[(4,6-dimethoxypyrimidin-2-yl)aminocarbonyl]-2-(1-methylethenyl)benzenesulfonamide | 50% |
| sodium alkylnaphthalenesulfonate | 2% |
| low viscosity methyl cellulose | 2% |
| diatomaceous earth | 46% |

The ingredients are blended, coarsely, hammer-milled and then air-milled to produce particles essentially all below 10 microns in diameter. The product is reblended before packaging.

EXAMPLE 19

Granule

| | |
|---|---|
| Wettable Powder of Example 18 | 5% |
| attapulgite granules (U.S.S. 20–40 mesh; 0.84–0.42 mm) | 95% |

A slurry of wettable powder containing 25% solids is sprayed on the surface of attapulgite granules in a double-cone blender. The granules are dried and packaged.

EXAMPLE 20

Extruded Pellet

| | |
|---|---|
| 2-(1-cyclopentenyl)-N—[(4-methoxy-6-methylpyrimidin-2-yl)aminocarbonyl]benzenesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 21

Oil Suspension

| | |
|---|---|
| N—[(4,6-dimethoxy-1,3,5-triazin-2-yl)aminocarbonyl]-2-(1-methylethenyl)benzenesulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 22

Wettable Powder

| | |
|---|---|
| N—[(4,6-dimethylpyrimidin-2-yl)aminocarbonyl]-2-(1-methylethenyl)benzenesulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 23

Low Strength Granule

| | |
|---|---|
| N—[(4,6-dimethylpyrimidin-2-yl)aminocarbonyl]-2-(1-methylethenyl)benzenesulfonamide | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 24

Aqueous Suspension

| | |
|---|---|
| 2-(1-cyclopentenyl)-N—[(4,6-dimethylpyrimidin-2-yl)-aminocarbonyl]benzenesulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 25

Solution

| | |
|---|---|
| N—[(4-methoxy-6-methyl-1,3,5-triazin-2-yl)aminocarbonyl]-2-(1-methylethenyl)benzenesulfonamide, sodium salt | 5% |
| water | 95% |

The salt is added directly to the water with stirring to produce the solution, which may then be packaged for use.

EXAMPLE 26

Low Strength Granule

| | |
|---|---|
| N—[(4,6-dimethoxy-1,3,5-triazin-2-yl)aminocarbonyl]-2-(1-methylethenyl)benzenesulfonamide | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 27

Granule

| | |
|---|---|
| 2-(1-cyclopentenyl)-N—[(4,6-dimethoxypyrimidin-2-yl)aminocarbonyl]benzenesulfonamide | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 28

High Strength Concentrate

| | |
|---|---|
| 2-(1-cyclopentenyl)-N—[(4-methoxy-6-methyl-1,3,5-triazin-2-yl)aminocarbonyl]benzenesulfonamide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 29

Wettable Powder

| | |
|---|---|
| 2-(1-cyclopentenyl)-N—[(4-methoxy-6-methylpyrimidin-2-yl)aminocarbonyl]benzenesulfonamide | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 30

Wettable Powder

| | |
|---|---|
| N—[(4-methoxy-6-methylpyrimidin-2-yl)aminocarbonyl]-2-(1-methylethenyl)benzenesulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 31

Oil Suspension

| | |
|---|---|
| 2-(1-cyclopentenyl)-N—[(4,6-dimethoxy-1,3,5-triazin-2-yl)aminocarbonyl]benzenesulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 miconrs. The product can be used directly, extended with oils, or emulsified in water.

UTILITY

The compounds of the present invention are active herbicides. They have utility for broad-spectrum pre- and/or post-emergence weed control in areas where complete control of all vegetation is desired, such as around fuel storage tanks, ammunition depots, industrial storage areas, oil-well sites, drive-in theaters, around billboards, highway and railroad structure. By properly selecting rate, time and method of application, compounds of this invention may also be used to modify plant growth beneficially, and also to selectively control weeds in crops such as wheat, barley, rice, soybeans and alfalfa.

The precise amount of the compounds of Formula I to be used in any given situation will vary according to the particular end result desired, the amount of foilage present, the weeds to be controlled, the crop species involved, the soil type, the formulation and mode of application, weather conditions, etc. Since so many variables play a role, it is not possible to state a rate of application suitable for all situations. Broadly speaking, the compounds of this invention are used at levels of about 0.05 to 20 kg/ha with a preferred range of 0.1 to 10 kg/ha. In general, the higher rates of application from within this range will be selected for adverse conditions or where extended persistence in soil is desired.

The compounds of Formula I may be combined with other herbicides and are particularly useful in combination with the ureas: such as 3-(3,4-dichlorophenyl)-1,1-diemthylurea (diuron); the triazines: such as 2-chloro-4-(ethylamino)-6-(isopropylamino)-s-triazine (atrazine); the uracils: such as 5-bromo-3-sec-butyl-6-methyluracil (bromacil); N-(phosponomethyl)glycine (glyphosate); 3-cyclohexyl-1-methyl-6-dimethylamino-s-triazine-2,4(1H,3H)-dione (hexazinone); N,N-dimethyl-2,2-diphenylacetamide (diphenamid); 2,4-dichlorophenoxyacetic acid (2,4-D) (and closely related compounds); 4-chloro-2-butynyl-3-chlorophenylcarbamate (barban); S-(2,3-dichloroallyl)-diisopropylthiocarbamate (diallate); S-(2,3,3-trichloroallyl-diisopropylthiocarbamate (triallate); 1,2-dimethyl-3,5-diphenyl-1H-pyrazolium methyl sulfate (difenzoquat methyl sulfate); methyl 2-[4-(2,4-dichlorophenoxy)phenoxy]propanoate (diclofop methyl); 4-amino-6-tert-butyl-3-(methylthio)-1,2,4-triazin-5(4H)-one (metribuzin); 3-(3,4-dichlorophenyl)-1-methoxy-1-methylurea (linuron); 3-isopropyl-1H-2,1,3-benzothiodiazin-4-(3H)-one-2,2-dioxide (bentazon); α,α,α-trifluoro-2,6-dinitro-N,N-dipropyl-p-toluidine (trifluralin); 1,1'-dimethyl-4,4'-bipyridinium ion (paraquate); monosodium methanearsonate (MSMA); 2-chloro-2',6'-diethyl (methoxymethyl)acetanilide (alachlor); and 1,1-dimethyl-3-(α,α,α-trifluoro-m-tolyl)-urea (fluometuron); and 5-(2-chloro-4-(trifluoromethyl)phenoxy]-2-nitrobenzoic acid, methyl ester (acifluorfenmethyl).

The activity of these compounds was discovered in a number of greenhouse tests. The tests are described and the data resulting from them are shown below.

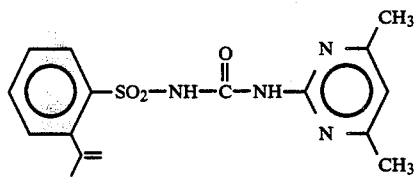

Compound 1

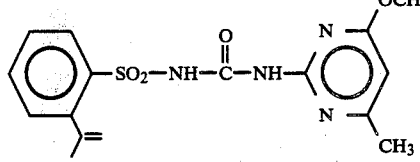

Compound 2

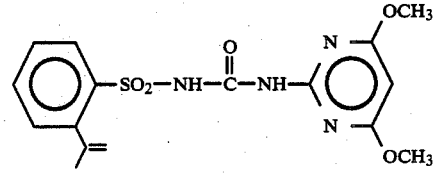

Compound 3

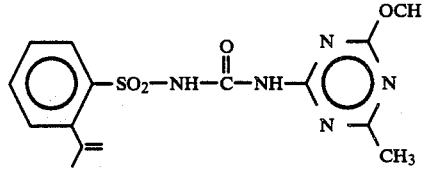

Compound 4

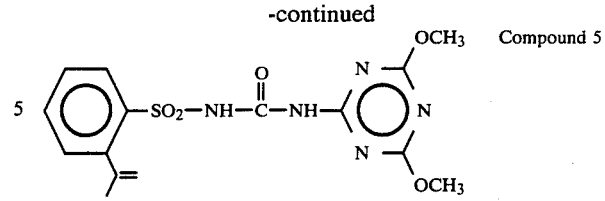

Compound 5

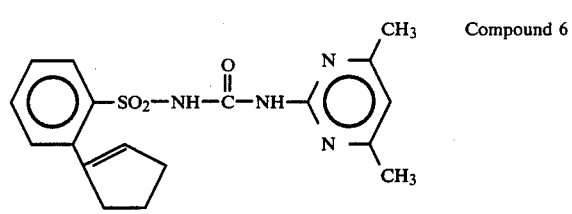

Compound 6

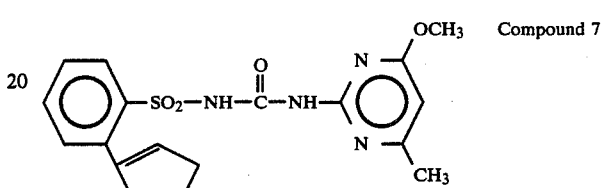

Compound 7

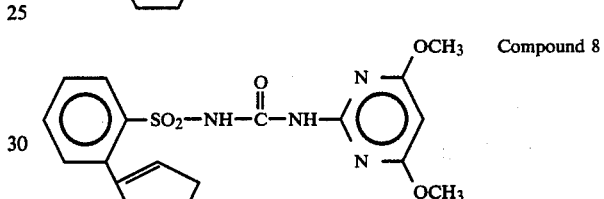

Compound 8

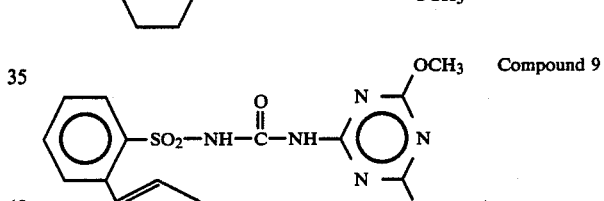

Compound 9

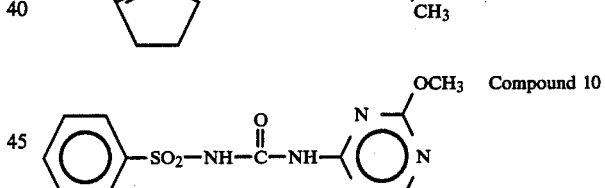

Compound 10

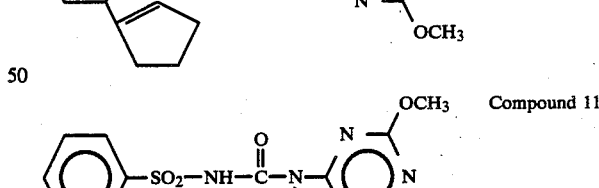

Compound 11

TEST A

Seeds of crabgrass (*Digitaria spp.*), barnyardgrass (*Echinochloa crusgalli*), wild oats (*Avena fatua*), cassia (*Cassia tora*), morningglory (*Ipomoea sp.*), cocklebur (*Xanthium spp.*), sorghum, corn, soybean, rice, wheat and nutsedge tubers (*Cyperus rotundus*) were planted in a growth medium and treated pre-emergence with the chemicals dissolved in a non phytotoxic solvent solution of the compounds of Table A. At the same time, cotton having five leaves (including cotyledonary ones), bush beans with the third trifoliate leaf expanding, crabgrass, barnyardgrass and wild oats with two leaves, cassia with three leaves (including cotyledonary ones), morningglory and cocklebur with four leaves (including the cotyledonary ones), sorghum and corn with four leaves, soybean with two cotyledonary leaves, rice with three leaves, wheat with one leaf, and nutsedge with three to five leaves were sprayed with a non-phytotoxic solvent solution of the compounds of Table A. Other containers of the above untreated weeds and crops were treated pre- or post-emergence with the same non-phytotoxic solvent so as to provide a solvent control. A set of untreated control plants was also included for comparison. Pre-emergence and post-emergence treated plants and controls were maintained in a greenhouse for sixteen days, then all treated plants were compared with their respective controls and rated visually for response to treatment.

The following rating system was used:
0 = no effect
10 = maximum effect
C = chlorosis or necrosis
D = defoliation
E = emergence inhibition
G = growth retardation
H = formative effects
S = albinism
U = unusual pigmentation
X = axillary stimulation
6Y = abscised buds or flowers It will readily be seen from the following that the tested compounds of the invention are active herbicides. Furthermore, certain of the compounds tested show selectivity as pre- and/or post-emergence herbicides in crops such as soybeans, rice and wheat.

TABLE A

| kg/ha | Compound 1 .05 | Compound 2 .05 | Compound 3 .05 | Compound 4 .05 | Compound 5 .05 | Compound 6 0.4 | .05 |
|---|---|---|---|---|---|---|---|
| POST-EMERGENCE | | | | | | | |
| BUSHBEAN | 6C,9G,6Y | 5C,9G,6Y | 9C | 9C | 9C | 3S,6G,6Y | 2S,5G,6Y |
| COTTON | 4C,9G | 5C,9G | 4C,9G | 9C | 9C | 3C,7G | 2C,5G |
| MORNINGGLORY | 6C,9G | 9C | 9C | 10C | 10C | 3C,6H | 2C,6H |
| COCKLEBUR | 9C | 3C,9G | 6G | 9C | 10C | 3C,5G | 2C,5G |
| CASSIA | 6C,9G | 6C,9G | 6C,9G | 9C | 9C | 2C | 2C |
| NUTSEDGE | 8G | 2C,8G | 4C,9G | 3G | 1C,7G | 2C,7G | 1C,5G |
| CRABGRASS | 2C,8G | 2C,8G | 1C,6G | 1C,5G | 1C,5G | 2C,5G | 1C,4G |
| BARNYARDGRASS | 6C,9G | 9C | 5C,9H | 9C | 3C,9H | 3C,9H | 5C,9H |
| WILD OATS | 3C,9G | 3C,7G | 1C,3G | 2G | 0 | 3C,7G,5X | 2C,5G |
| WHEAT | 3C,9G | 3C,8G | 1C,7G | 0 | 0 | 5G | 5G |
| CORN | 2U,9G | 5C,9G | 4C,8H | 5U,9G | 3U,9G | 3C,7G | 1C,3H |
| SOYBEAN | 9C | 6C,9G | 9C | 6C,9G | 6C,9G | 1H | 1C |
| RICE | 6C,9G | 9C | 3C,9G | 5C,7G | 2C,6G | 8G | 2C,7G |
| SORGHUM | 2C,9G | 2C,9G | 2C,8H | 2C,9G | 2C,7G | 2C,8G | 3C,8H |
| PRE-EMERGENCE | | | | | | | |
| MORNINGGLORY | 9G | 9G | 9G | 9C | 9C | 8G | 8G |
| COCKLEBUR | 9H | 9H | 9H | 9H | 8H | 8H | 9H |
| CASSIA | 9G | 9G | 7G | 9G | 8G | 5G | 1C |
| NUTSEDGE | 10E | 10E | 10E | 5G | 5G | 9G | 2C,8G |
| CRABGRASS | 3C,8G | 4C,8G | 2C,8G | 1C | 0 | 3G | 2G |
| BARNYARDGRASS | 9H | 5C,9H | 9H | 3C,9H | 3C,8H | 5C,9H | 2C,9H |
| WILD OATS | 2C,8G | 2C,8G | 8G | 2C,6G | 4G | 9H | 2C,9H |
| WHEAT | 9H | 1C,9H | 1C,9G | 3G | 0 | 9H | 1C,8G |
| CORN | 9G | 9G | 1U,9H | 9G | 3C,9H | 2C,9H | 2C,8H |
| SOYBEAN | 9H | 9H | 8H | 9H | 9H | 2H | 2G |
| RICE | 10E | 10E | 10E | 2C,6G | 3G | 9H | 3C,9H |
| SORGHUM | 6C,9G | 5C,9H | 1C,9G | 2C,9H | 2C,7G | 4C,9H | 2C,9G |

| kg/ha | Compound 7 0.4 | Compound 8 .05 | Compound 8 0.4 | .05 | Compound 9 0.4 | .05 | Compound 10 0.4 | .05 | Compound 11 0.4 | .05 |
|---|---|---|---|---|---|---|---|---|---|---|
| POST-EMERGENCE | | | | | | | | | | |
| BUSHBEAN | 5S,8G,6Y | 4S,6G,6Y | 5S,9G,6Y | 4S,8G,6Y | 9C | 9C | 9C | 9C | 2C,2H | 1C |
| COTTON | 3C,4H | 2C,2H | 2C,5G | 3C,7G | 5C,9G | 3C,7G | 5C,9G | 6C,9G | 2C,2H | 1C |
| MORNINGGLORY | 3C,9G | 2C,6G | 5C,9H | 3C,6G | 10C | 10C | 5C,9G | 9C | 2C,4G | 2C |
| COCKLEBUR | 3C,5H | 2C,5H | 4C,9H | 2C,7G | 9C | 9C | 6C,9G | 6C,9G | 3C,7G | 2C |
| CASSIA | 2C,5G | 2C, | 2C,3H | 2C | 3C,6G | 2C | 3C,8G | 3C,7G | 2C | 1C |
| NUTSEDGE | 8G | 2C,8G | 8G | 2C,7G | 1C,4G | 0 | 1C | 0 | 0 | 0 |
| CRABGRASS | 2C,4H | 1C,3G | 1C,5H | 1C | 2C | 0 | 2G | 0 | 0 | 0 |
| BARNYARDGRASS | 6C,9H | 3C,9H | 3C,9H | 3C,9H | 3C,6H | 3H | 2C,5H | 1C,2H | 0 | 0 |
| WILD OATS | 2C,7G,8X | 1C,4G,5X | 1C,4G,5X | 0 | 0 | 0 | 0 | 0 | 0 | 0 |
| WHEAT | 1C,5G | 2G | 3G | 0 | 0 | 0 | 0 | 0 | 0 | 0 |
| CORN | 8H | 2C,7H | 1C,4G | 1C,2G | 2G | 2G | 0 | 0 | 0 | 0 |
| SOYBEAN | 1C,1H | 1C,1H | 3C,6H | 1C,4H | 5C,9G | 1C,5G | 5C,9G | 3C,8G | 2C,2H | 1C,1H |
| RICE | 2C,8H | 2C,5G | 8G | 1C,7G | 1C,5G | 0 | 2G | 2G | 0 | 0 |
| SORGHUM | 3C,8H | 3C,7H | 2C,9H | 2C,6G | 1C,8G | 2G | 2C,5G | 2C | 0 | 0 |
| PRE-EMERGENCE | | | | | | | | | | |
| MORNINGGLORY | 9G | 9G | 8G | 8G | 9C | 9C | 10C | 9C | 2G | 0 |
| COCKLEBUR | 2C,8H | — | 9H | 9H | 9H | 9H | 9H | 9H | 5H | 3H |
| CASSIA | 2C,6G | 1C | 1H | 1C | 9G | 6G | 9G | 5G | 0 | 0 |
| NUTSEDGE | 10E | 3C,9G | 10E | 10E | 5G | 0 | 6G | 0 | 0 | 0 |
| CRABGRASS | 1C,5G | 2C,5G | 1C,3G | 2G | 2G | 0 | 2G | 1C | 0 | 0 |
| BARNYARDGRASS | 5C,9H | 5C,9H | 3C,9H | 2C,9H | 2C,8H | 3C,5G | 3C,9G | 3C,7G | 0 | 0 |
| WILD OATS | 2C,8G | 2C,9G | 2C,7H | 2C,7G | 1C,3G | 5G | 3C | 1C,3G | 0 | 0 |
| WHEAT | 3C,8G | 3C,8G | 1C,7G | 1C,7G | 2G | 0 | 0 | 0 | 0 | 0 |

TABLE A-continued

| | | | | | | | | | | |
|---|---|---|---|---|---|---|---|---|---|---|
| CORN | 2C,9G | 4C,8H | 3C,8G | 2C,7G | 2C,9H | 2C,6G | 3C,8G | 3C,7G | 1C,4G | 2G |
| SOYBEAN | 2C,3H | 2C,3H | 2C,5H | 2C,3H | 2C,2H | 1C | 1C,2H | 0 | 1H | 0 |
| RICE | 3C,8H | 4C,8H | 5C,9H | 4C,9H | 3C,7G | 2C | 2C,6G | 1C,5G | 1C | 0 |
| SORGHUM | 4C,9G | 3C,9G | 2C,9G | 1C,9G | 9G | 2C,6H | 2C,8G | 2C,7G | 0 | 0 |

TEST B

Two plastic bulb pans were filled with fertilized and limed Fallsington silt loam soil. One pan was planted with corn, sorghum, Kentucky bluegrass and several grassy weeds. The other pan was planted with cotton, soybeans, purple nutsedge (*Cyperus rotundus*), and several broadleaf weeds. The following grassy and broadleaf weeds were planted: crabgrass (*Digitaria sanguinalis*), barnyardgrass (*Echinochloa crusgalli*), wild oats (*Avena fatua*), johnsongrass (*Sorghum halepense*), dallisgrass (*Paspalum dilatatum*), giant foxtail (*Setaria faberii*), cheatgrass (*Bromus secalinus*), mustard (*Brassica arvensis*), cocklebur (*Xanthium pensylvanicum*), pigweed (*Amaranthus retroflexus*), morningglory (*Ipomoea hederacea*), cassia (*Cassia tora*), teaweed (*Sida spinosa*), velvetleaf (*Abutilon theophrasti*), and jimsonweed (*Datura stramonium*). A 12.5 cm diameter plastic pot was also filled with prepared soil and planted with rice and wheat. Another 12.5 cm pot was planted with sugarbeets. The above four containers were treated pre-emergence with several test compounds within the scope of the invention.

Twenty-eight days after treatment, the plants were evaluated and visually rated for response to the chemical treatments utilizing the rating system described previously for Test A. The data are summarized in Table B.

At the very low rates of application selected for this test and, moreover, when applied to soil rather than sand, the compounds retain their herbicidal properties. It will be noted that several of the compounds have utility for selective pre-emergence weed control in crops, e.g. wheat.

TABLE B

| PRE-EMERGENCE OF FALLSINGTON SILT LOAM | | | | | | | | | | | |
|---|---|---|---|---|---|---|---|---|---|---|---|
| | Compound 1 | | Compound 2 | | Compound 3 | | Compound 4 | | Compound 5 | | Compound 6 |
| Rate kg/ha | 0.03 | 0.12 | 0.03 | 0.12 | 0.03 | 0.12 | 0.03 | 0.12 | 0.03 | 0.12 | 0.03 |
| Crabgrass | 0 | 0 | 3G | 4G | 0 | 0 | 0 | 0 | 0 | 0 | 0 |
| Barnyardgrass | 3H,7G | 3H,7G | 8G,5H | 8G,5H | 4G | 7G,3H | 4G,3C | 6G,3C | 3G | 6G,4C | 4G |
| Sorghum | 9G,9C | 9G,9C | 7G,3H | 9G,8C | 3G | 0 | 4G | 8G,5H | 0 | 3G | 3G |
| Wild Oats | 3G | 5G | 4G | 6G | 0 | 0 | 3G | 4G | 0 | 3G | 6G |
| Johnsongrass | 5G | 6G,3H | 5G | 8G,5H | 3G,3H | 3G,3H | 4G,2H | 4G,2H | 3G | 2G | 4G |
| Dallisgrass | 4G | 6G | 3G | 6G | 0 | 0 | 3G | 3G | 5G | 3G | 3G |
| Giant foxtail | 3G | 4G,3H | 5G,3H | 8G,8H | 3G,3H | 4G,3H | 3G,2H | 5G,2H | 3G | 3G | 0 |
| Ky. bluegrass | 4G,3H | 5G,3H | 4G,3H | 5G,3H | 5G,3H | 6G,5H | 5G | 5G | 4G | 5G | 3G |
| Cheatgrass | — | 5G | 5G | 7G | 0 | 3G | 5G,3H | 5G | 0 | 3G | 6G |
| Sugarbeets | 9G,9C | 9G,9C | 8G,6C | 10C | 8G,8C | 8G,7C | 9G,9C | 10C | 9G,9C | 10C | 3G |
| Corn | 5G | 7G,5H | 3G | 6G,5H | 0 | 0 | 5G,2H | 7G,5H | 3G | 7G,5H | 2G |
| Mustard | 7G,5C | 8G,7C | 9G,9C | 9G,9C | 8G,8C | 9G,8C | 9G,9C | 9G,9C | 9G,9C | 9G,9C | 8G,5C |
| Cocklebur | 6G | 6G,3H | 4G | 6G,3C | 3G | 4G | 6G,3H | 9G,9C | 6G,3H | 6G,3H | 0 |
| Pigweed | — | — | — | — | — | — | 10C | 8G,8C | 3G | 10C | 8G,5C |
| Nutsedge | — | — | 0 | 0 | — | — | 6G | 7G | 5G | 6G | 3G |
| Cotton | 3G | 7G | 5G,3H | 5G,3H | 3G | 5G,3H | 8G,8C | 9G,9C | 7G,3H | 8G,8C | 4G |
| Morningglory | 6G,5H | 8G,5H | 3G | 4G,3H | 0 | 0 | 8G,8C | 8G,8C | 8G,5C | 8G,8C | 4G |
| Cassia | 8G | 7G,5C | 7G,5C | 9G,9C | 5G,3C | 7G,3C | 8G,5C | 8G,5C | 8G,5C | 8G,9C | 3G |
| Teaweed | 10E | 10E | 10E | 10E | 0 | 5G,5C | 5G,2C | 8G,8C | 7G,5C | 10C | 0 |
| Velvetleaf | 7G,5H | 9G,5C | 7G,3H | 8G,5C | 3G | 7G,5H | 8G,8C | 10C | 6G,3H | 7G,5H | 3G |
| Jimsonweed | 7G,8C | 7G,5C | 8G,9C | 8G,8C | — | 0 | 7G,5C | 7G,7C | 6G,5C | 7G,5C | 3G |
| Soybean | 5G,3H | 5G,2H | 5G,3C | 6G,3H | 0 | 5G | 9G,9C | 9G,9C | 9G,5H | 9G,9C | 3G |
| Rice | 10E | 10E | 8G | 8G,8C | 3G | 7G,3H | 3G | 5G,3H | 3G | 5G | 4G |
| Wheat | 2G | 5G | 4G | 5G | 0 | 3G | 0 | 3G | 0 | 3G | 0 |

| | Compound 6 | Compound 7 | | Compound 8 | | Compound 9 | | Compound 10 | | Compound 11 | |
|---|---|---|---|---|---|---|---|---|---|---|---|
| Rate kg/ha | 0.12 | 0.03 | 0.12 | 0.03 | 0.12 | 0.03 | 0.12 | 0.03 | 0.12 | 0.03 | 0.12 |
| Crabgrass | 3G | 0 | 3G | 0 | 0 | 0 | 0 | 0 | 3G | 0 | 0 |
| Barnyardgrass | 4G | 5G | 7G,2C | 3G | 4G | 0 | 3G | 0 | 2G | 0 | 2G |
| Sorghum | 5G,3H | 5G,3H | 7G,5H | 3G | 3G | 3G | 3G | 0 | 2G | 0 | 3G |
| Wild Oats | 5G | 4G | 6G | 0 | 3G | 3G | 4G | 0 | 0 | 0 | 0 |
| Johnsongrass | 5G | 5G | 5G | 3G | 3G | 3G | 4G | 0 | 0 | 0 | 0 |
| Dallisgrass | 3G | 5G | 5G | 4G | 4G | 3G | 3G | 0 | 0 | 0 | 3G |
| Giant foxtail | 3G | 4G | 4G | 3G | 4G | 0 | 0 | 0 | 0 | 0 | 0 |
| Ky. bluegrass | 6G | 6G | 7G,5C | 5G | 7G,3H | 4G | 3G | 0 | 3G | 0 | 2G |
| Cheatgrass | 8G | 8G | 8G | 5G | 7G | 7G | 2G | 0 | 0 | 0 | 0 |
| Sugarbeets | 8G,9C | 7G,7C | 7G,7C | 4G | 6G,3H | 6G | 10E | 7G,7C | 7G,7C | 3G | 0 |
| Corn | 3G | 2G | 3G | 4G | 2G | 0 | 3C | 0 | 0 | 0 | 0 |
| Mustard | 7G,3C | 9G,8C | 10C | 6G | 8G,8C | 6G,3C | 10C | 5G | 7G,4C | 0 | 4G |
| Cocklebur | 4G | 2G | 6G,3H | 3G | 2H | 4G | 6G | 2G | 6G | 0 | 0 |
| Pigweed | 10E | 10E | 10E | 8G,8C | 10E | 8G,9C | 10E | 8G,5C | 9G,8C | 0 | 2G |
| Nutsedge | 3G | 0 | 3G | 3G | 3G | 0 | 4G | 0 | 4G | 0 | 0 |
| Cotton | 4G | 4G | 6G | 4G | 3G | 5G | 7G | 3G | 5G | 0 | 0 |
| Morningglory | 3G | 4G | 3G | 3G | 4G | 7G,3C | 8G,3C | 7G,4C | 9G,7C | 0 | 0 |
| Cassia | 5G | 0 | 3G | 0 | 4G | 0 | 2G | 0 | 5G | 0 | 0 |
| Teaweed | 0 | 2G | 5G,3C | 0 | 3G | 0 | 0 | 0 | 3G | 0 | 0 |
| Velvetleaf | 5G,3C | 4G,2H | 5G,5H | 2G | 5G,3H | 0 | 3G,2H | 0 | 2G | 0 | 0 |
| Jimsonweed | 4G | 4G | 6G,3C | 0 | 5G | 0 | 0 | 2G | 3G | 0 | 0 |
| Soybean | 2G | 3G | 3G,2H | 3G | 0 | 0 | 0 | 0 | 0 | 0 | 0 |

TABLE B-continued

| | PRE-EMERGENCE OF FALLSINGTON SILT LOAM | | | | | | | | | | |
|---|---|---|---|---|---|---|---|---|---|---|---|
| Rice | 6G,3H | 3G | 5G,3H | 3G | 3G,2H | 0 | 0 | 0 | 0 | 0 | 0 |
| Wheat | 0 | 0 | 3G | 0 | 0 | 0 | 0 | 0 | 0 | 0 | 0 |

TEST C

The test chemicals, dissolved in a nonphytotoxic solvent, were applied in an overall spray to the foilage and surrounding soil of selected plant species. One day after treatment, plants were checked for rapid burn injury. Approximately fourteen days after treatment all species were visually compared to untreated controls and rated for response to treatment. The rating system was as described previously for Test A. The data are presented in Table C.

All plant species were seeded in Woodstown sandy loam soil and grown in a greenhouse, The following species were grown in soil contained in plastic pots (25 cm diameter by 13 cm deep): soybeans, cotton, alfalfa, corn, rice, wheat, sorghum, velvetleaf (*Abutilon theophrasti*), sesbania (*Sesbania exaltata*), Cassia (*Cassia tora*), morningglory (*Ipomoea hederacea*), jimsonweed (*Datura stramonium*) cocklebur (*Xanthium pensylvanicum*), crabgrass (*Digitaria spp.*), nutsedge (*Cyperus rotundus*), barnyardgrass (*Echinochloa crusgalli*), giant foxtail (*Setaria faberii*), and wild oats (*Avena fatua*). The following species were grown in soil in a paper cup (12 cm diameter by 13 cm deep): sunflower, sugarbeets, and mustard. All plants were sprayed approximately 14 days after planting. Additional plant species are sometimes added to this standard test in order to evaluate unusual selectivity.

The compounds tested by this precedure show a generally high level of post-emergence activity. Several of the compounds also show selectivity in the post-emergence control of weeds in crops such as alfalfa and rice.

TEST D

Two ten-inch in diameter plastic pans lined with polyethylene liners were filled with prepared Fallsington slit loam soil. One pan was planted with seeds of wheat (*Triticum aestivum*), barley (*Hordeum vulgare*), wild oats (*Avena fatua*), downy brome (*Bromus tectorum*), cheatgrass (*Bromus secalinus*), blackgrass (*Alopecurus myosuroides*), annul bluegrass (*Poa annua*), green foxtail (*Setaria viridis*), quackgrass (*Agropyron repens*), Italian ryegrass (*Lolium multiflorum*) and ripgut brome (*Bromus rigidus*). The other pan was planted with seeds of Russian thistle (*Salsola kali*), tansy mustard (*Descuraina pinnata*), smartweed (*Polygonum pennsylvanicum*), tumble mustard (*Sisymbrium altissium*) kochia (*Kochia scoparia*), shepherd's purse (*Capsella bursa-pastoris*), Matricaria inodora, black nightside (*Solanum nigrum*), yellow rocket (*Barbarea vulgaris*), wild mustard (*Brassica kaber*) and wild buckwheat (*Polygonum convolvulus*). The above two pans were treated pre-emergence. At the same time two pans in which the above plant species were growing were treated post-emergence. Plant height at the time of treatment ranged from 1–15 cm depending on plant species.

The compounds applied were diluted with a non-phytotoxic solvent and sprayed over-the-top of the pans. An untreated control and a solvent alone control were included for comparison. All treatments were maintained in the greenhouse for 20 days at which time the treatments were compared to the controls and the effects visually rated as described for Test A. The recorded data are presented in Table D. The compounds demonstrated good pre- and post-emergence control of several troublesome weed species found in cereal crops, e.g. wheat and barely.

TABLE C

| | Compound 1 | | Compound 2 | | Compound 3 | | Compound 4 | | | | Compound 5 | | | |
|---|---|---|---|---|---|---|---|---|---|---|---|---|---|---|
| Rate kg/ha | 0.06 | 0.015 | 0.06 | 0.015 | 0.06 | 0.015 | 0.25 | 0.06 | 0.015 | 0.004 | 0.25 | 0.06 | 0.015 | 0.004 |
| Soybeans | 10C | 10C | 10C | 10C | 10C | 10C | 10C | 10C | 9G,9C | 9G,9C | 10G,9C | 10C | 10C | 10C |
| Velvetleaf | 10C | 9G,9C | 10C | 10C | 10C | 9G,7C | 10C | 9G,9C | 9G,9C | 9G,9C | 10C | 10C | 7G,6C | 7G,6C |
| Sesbania | 10C | 10C | 10C | 10C | 10C | 10C | 10C | 10C | 10C | 10C | 10C | 10C | 10C | 8G,8C |
| Cassia | 7G | 5G,2C | 10C | 5G,3C | 7G,5C | 8G,1C | 10C | 9G,9C | 9G,9C | 7G,4C | 9G,9C | 9G,9C | — | 7G,1C |
| Cotton | 9G,2C | 8G,3C | 10C | 8G,2C | 9G,9C | 10C | 10C | 10C | 9G,9C | 10C | 10C | 10C | 9G,9C | 6G,4C |
| Morningglory | 9G,2C | 4G,2C | 7G,3C | 5G,1C | 10C | 9G,5C | 10C | 9G,8C | 9G,8C | 6G,4C | 10C | 10C | 9G,8C | 7G,4C |
| Alfalfa | 10C | 4G | 8G,6C | 5G,2C | 9G,7C | 4G,4C | 9G,9C | 9G,9C | 8G,8C | 1G | 9G,9C | 3G | 3G,1C | 1G |
| Jimsonweed | — | 4G | 4G | 2G | 4G | 1G | 8C | 7C | 1C | 1C | 6C | 5C | 1C | 0 |
| Cocklebur | 10C | 7G | 9G,2H | 8G,1H | 6G | 3G | 9G,9C | 10C | 8G,4C | 5G,1C | 10C | 8G,8C | 5G,1C | 5G |
| Corn | 7G,1U | 6G,4H | 7G,1U | 6H,1C | 6G,4H | 5G,1H | 9G,3C | 9G,IU | 8G,4H | 3G,1C | 9G,2H | 5G,1H | 3G,1C | 0 |
| Crabgrass | 8G | 4G | 8G | 7G | 6G | 2G | 5G,2C | 2C | 2C | 1G | 5G,2C | 1C | 1C | 0 |
| Rice | 9G,4C | 8G,4C | 8G,6C | 8G,4C | 8G,4C | 7G | 9G,2C | 6G,2C | 5G,1C | 2G | 4G | 4G | 1G | 0 |
| Nutsedge | 5G | 1G | 5G | 0 | 6G | 5G | 8G,1C | 2G | 0 | 2G | 2G | 0 | 0 | 0 |
| Barnyardgrass | 8G,6C | 8G,1C | 9G,5C | 9G,2C | 7G | 9G,1C | 9G,9C | 9G,9C | 8G,5C | 4G,4C | 9G,9C | 9G,9C | 4G,2C | 1C |
| Wheat | 7G,2C | 7G | 8G,3C | 6G | 9G,1C | 7G | 5G | 3G | 0 | 0 | 4G | 2G | 1G | 0 |
| Giant Foxtail | 8G,3C | 6G,3C | 8G,1C | 8G,1C | 9G,7C | 6G | 8G,6C | 5G | 0 | 0 | 6G | 5G,1C | 1C | 0 |
| Wild Oats | 8G,4C | 7G | 8G,1C | 8G,1C | 7G,3C | 6G | 6G,2C | 4G | 2G | 1G | 4G | 1G | 1G | 0 |
| Sorghum | 7G,3C | 7G,1C | 8G,2C | 7G,2C | 6G,1C | 0 | 9G,1U | 8G,1U | 4G,2C | 4G | 5G,1C | 4G | 3G | 1G |
| Mustard | 10C | 8G | 10C | 8G,7C | 10C | 9G,8C | 10C | 10C | 10C | 10C | 10C | 10C | 10C | 9G,8C |
| Pigweed | — | — | — | — | — | — | — | — | — | — | — | — | — | — |
| Johnsongrass | — | — | — | — | — | — | — | — | — | — | — | — | — | — |
| Sunflower | 10C | 9G | 8G,5C | 8G | 10C | 7G,3C | 10C | 10C | 10C | 10C | 10C | 10C | 10C | 10C |
| Sugarbeets | 9G,2C | 6G | 8G | 6G | 7G,3C | 8G | 10C | 9G,9C | 9G,9C | 9G,9C | 9G,9C | 9G,7C | 9G,7C | 9G,7C |

TABLE D

| | Compound 4 | | | | Compound 5 | | | |
|---|---|---|---|---|---|---|---|---|
| Rate kg/ha | Post-emergence 0.015 | Pre-emergence 0.015 | Post-emergence 0.06 | Pre-emergence 0.06 | Post-emergence 0.015 | Pre-emergence 0.015 | Post-emergence 0.06 | Pre-emergence 0.06 |
| wheat | 3G | 4G | 4G | 3G | 1G | 2G | 1G | 4G |
| barley | 1C,2G | 1C,1G | 3C,3G | 1C,3G | 0 | 0 | 0 | 1G |
| wild oats | 2C,2G | 1C,5G | 2C,2G | 5G | 0 | 2G | 0 | 3G |
| downy brome | 7G | 6G | 1C,7G | 8G | 0 | 1G | 2G | 2G |
| cheatgrass | 5G | 6G | 7G | 8G | 2G | 1C,2G | 1C,4G | 3G |
| blackgrass | 5C,8G | 6G | 10C | 9C,9G | 1C,1G | 1C,3G | 3C,6G | 1C,3G |
| annual bluegrass | 7C,7G | — | 10C | — | 0 | — | 1G | — |
| green foxtail | 1C,6G | 1C,2G | 3C,8G | 3C,5G | 4G | 0 | 1C,6G | 2C,1G |
| quackgrass | 1C,4G | 1G | 2C,7G | 2G | 3G | 3G | 2C,6G | 3G |
| Italian ryegrass | 3C,5G | 3G | 5C,5G | 1C,6G | 1C,2G | 3G | 2C,4G | 5G |
| ripgut brome | 1C,5G | 2G | 3C,6G | 3G | 3G | 1G | 3C,3G | 2G |
| Russian thistle | 9C,9G | 2G | 10C | 1C,2G | 9C,9G | 3G | 9C,9G | 3G |
| tansy mustard | 10C | 10C | 10C | 10C | 10C | 10C | 10C | 10C |
| smartweed | — | — | — | — | — | — | — | — |
| jimhill mustard | 10C | 5C,9G | 10C | 9C,9G | 10C | 5C,9G | 10C | 10C |
| Kochia | 10C | 8G | 10C | 8C,8G | 2C | 6G | 4C,6G | 7G |
| shepherd's purse | 10C | 10C | 10C | 10C | 10C | 10C | 10C | 10C |
| false chamomile | 10C | 9G | 10C | 9G | 10C | 9G | 10C | 9G |
| black nightshade | 3C,7G | 6G | 9C,9G | 8G | 2C,4G | 5C,7G | 2C,6G | 5C,8G |
| yellow rocket | 10C | 9G | 10C | 9C,9G | 5C,7G | 8G | 5C,7G | 9G |
| wild mustard | 10C | 9C,9G | 10C | 10C | 10C | 9C,9G | 10C | 9C,9G |
| wild buckwheat | 9C,9G | 2C,5G | 10C | 3C,7G | 8C,8G | 1C,4G | 9C,9G | 1C,6G |

What is claimed is:

1. A compound selected from

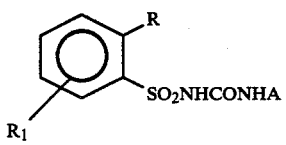

wherein
R is

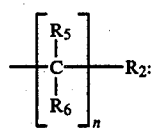

$R_2$ is $C_2$-$C_5$ alkenyl, $C_5$-$C_6$ cycloalkenyl or $C_2$-$C_3$ alkenyl substituted with 1-3 chlorine atoms;
n is 0 or 1;
$R_1$ is H, F, Cl, Br, $NO_2$, $CF_3$, $C_1$-$C_4$ alkyl, $OCF_3$ or $C_1$-$C_3$ alkoxy;
$R_5$ and $R_6$ are independently H or $CH_3$;
A is

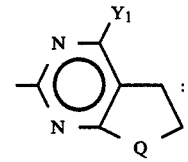

$Y_1$ is H, $CH_3$, $OCH_3$ or Cl; and
Q is $CH_2$.

2. A compound of claim 1 wherein $R_1$ is H.

3. A compound of claim 2 wherein $Y_1$ is $CH_3$ or $OCH_3$.

4. A compound of claim 2 wherein $R_5$ and $R_6$ are H.

5. A composition suitable for controlling the growth of undesired vegetation which comprises an effective amount of a compound of claim 1 and at least one of the following: surfactant, solid or liquid diluent.

6. A composition suitable for controlling the growth of undesired vegetation which comprises an effective amount of a compound of claim 2 and at least one of the following: surfactant, solid or liquid diluent.

7. A composition suitable for controlling the growth of undesired vegetation which comprises an effective amount of a compound of claim 3 and at least one of the following: surfactant, solid or liquid diluent.

8. A method for controlling the growth of undesired vegetation which comprises applying to the locus to be protected an effective amount of a compound of claim 1.

9. A method for controlling the growth of undesired vegetation which comprises applying to the locus to be protected an effective amount of a compound of claim 2.

10. A method for controlling the growth of undesired vegetation which comprises applying to the locus to be protected an effective amount of a compound of claim 3.

* * * * *